(12) United States Patent (10) Patent No.: US 8,394,639 B2
Dihazi et al. (45) Date of Patent: Mar. 12, 2013

(54) BIOMARKERS FOR RENAL DISEASE

(75) Inventors: Hassan Dihazi, Göttingen (DE); Gerhard A. Müller, Göttingen (DE); Frank Strutz, Mainz (DE)

(73) Assignee: Georg-August-Universitat Gottingen Stiftung Offentlichen Rechts, Universitatsmedizin, Gottingen (DE)

( * ) Notice: Subject to any disclaimer, the term of this patent is extended or adjusted under 35 U.S.C. 154(b) by 613 days.

(21) Appl. No.: 12/504,429

(22) Filed: Jul. 16, 2009

(65) Prior Publication Data

US 2010/0035263 A1   Feb. 11, 2010

Related U.S. Application Data

(60) Provisional application No. 61/135,233, filed on Jul. 17, 2008.

(51) Int. Cl.
*G01N 33/00* (2006.01)
*G01N 24/00* (2006.01)
*C12Q 1/68* (2006.01)

(52) U.S. Cl. ............ 436/86; 436/63; 436/94; 436/173; 435/6.1

(58) Field of Classification Search ................ None
See application file for complete search history.

(56) References Cited

U.S. PATENT DOCUMENTS 5,359,681 A   10/1994 Jorgensen et al.
2011/0111424 A1*   5/2011 Rush et al. .................... 435/7.1

OTHER PUBLICATIONS

56 Facts About Blood [online][retrieved on Mar. 25, 2012] retrieved from http://www.americasblood.org/go.cfm?do=page.view&pid=12.*
Bradford, MM. A rapid and sensitive method for the quantitation of microgram quantities of protein utilizing the principle of protein-dye binding. Anal Biochem 1976;72:248-54.
De Bont JM, den Boer ML, Reddingius RE, Jansen J, Passier M, van Schaik RH, et al. Identification of apolipoprotein A-II in cerebrospinal fluid of pediatric brain tumor patients by protein expression profiling. Clin Chem 2006;52:1501-9.
Dihazi H, Asif AR, Agarwal NK, Doncheva Y, Muller GA. Proteomic analysis of cellular response to osmotic stress in thick ascending limb of Henle's loop (TALH) cells. Mol Cell Proteomics 2005;4:1445-58. (Dihazi 2005b).
Dihazi H, Muller GA. Urinary proteomics: a tool to discover biomarkers of kidney diseases. Expert Rev Proteomics 2007;4:39-50.
Dihazi H, Sandra Lindner, Markus Meyer, Asif Abdul Rahman, Gerhard Anton Mueller and Frank Strutz. Characterization of diabetic nephropathy by urinary proteomic analysis: identification of Biomarkers. 3rd World Congress of Nephrology, 2005. (Dihazi 2005a).
Dihazi H. Clinical proteomics: an insight into the urinary proteome. Interview with Dr. Hassan Dihazi. Expert Rev Proteomics 2006;3:481-2.
Hong CY, Chia KS. Markers of diabetic nephropathy. J Diabetes Complications 1998;12:43-60.
Hong CY, Hughes K, Chia KS, Ng V, Ling SL. Urinary alpha1-microglobulin as a marker of nephropathy in type 2 diabetic Asian subjects in Singapore. Diabetes Care 2003;26:338-42.
Muller GA, Muller CA, Dihazi H. Clinical proteomics—on the long way from bench to bedside? Nephrol Dial Transplant 2007, 22:1297-1300.
Mykkanen L, Haffner SM, Kuusisto J, Pyorala K, Laakso M. Microalbuminuria precedes the development of NIDDM. Diabetes 1994;43:552-7.
Rossing K, Mischak H, Parving HH, Christensen PK, Walden M, Hillmann M, Kaiser T. Impact of diabetic nephropathy and angiotensin II receptor blockade on urinary polypeptide patterns. Kidney Int 2005;68:193-205.
Schardijn GH, Statius van Eps LW. Beta 2-microglobulin: its significance in the evaluation of renal function. Kidney Int 1987;32:635-41.
Schaub S, Rush D, Wilkins J, Gibson IW, Weiler T, Sangster K, et al. Proteomic-based detection of urine proteins associated with acute renal allograft rejection. J Am Soc Nephrol 2004;15:219-27.
Shevchenko A, Wilm M, Vorm O, Mann M. Mass spectrometric sequencing of proteins silver-stained polyacrylamide gels. Anal Chem 1996;68:850-8.
Sun L, Pan X, Wada J, Haas CS, Wuthrich RP, Danesh FR, et al. Isolation and functional analysis of mouse UbA52 gene and its relevance to diabetic nephropathy. J Biol Chem 2002;277:29953-62.
Susztak K, Bollinger EP. Diabetic nephropathy: a frontier for personalized medicine. J Am Soc Nephrol 2006;17:361-7.
Thongboonkerd V, Barati MT, McLeish KR, Pierce WM, Epstein PN, Klein JB. Proteomics and diabetic nephropathy. Contrib Nephrol 2004;141:142-54.
Thongboonkerd V, Malasit P. Renal and urinary proteomics: current applications and challenges. Proteomics 2005;5:1033-42.
Tolson JP, Flad T, Gnau V, Dihazi H, Hennenlotter J, Beck A, et al. Differential detection of S100A8 in transitional cell carcinoma of the bladder by pair wise tissue proteomic and immunohistochemical analysis. Proteomics 2006;6:697-708.
Dihazi H et al, Characterization of Diabetic Nephropathy by Urinary Proteomic Analysis: Identification of a Processed Ubiquitin Form as a Differantially Excreted Protein in Diabetic Nephropathy Patients, ClinChem, 2007, 53:9, 1636-1645.
Sackett et al., Clinical Epidemiology: A Basic Science for Clinical Medicine, Little Brown & Co., 1985, pp. 106-107.
Schardijn, GH et al., Urinary beta-2-microglobulin in upper and lower urinary-tract infections. Lancet 1979; 1:805-07.

* cited by examiner

*Primary Examiner* — Samuel Woolwine
(74) *Attorney, Agent, or Firm* — Brinks, Hofer, Gilson & Lione

(57) ABSTRACT

The invention provides methods and kits for diagnosing a renal disease in a patient or for predicting the risk of a patient for developing a renal disease. In one embodiment, the invention provides a method for diagnosing a renal disease in a patient, comprising determining the level of a ubiquitin fragment having a mass-to-charge ratio (m/z) of 6188 (ubiquitin m/z 6188), or the level of a nucleic acid encoding ubiquitin m/z 6188, in a sample derived from said patient, wherein the substantial absence or a reduced level of less than 25% of ubiquitin m/z 6188 or the nucleic acid encoding ubiquitin m/z 6188 compared to a control is indicative of the renal disease in said patient.

11 Claims, 13 Drawing Sheets

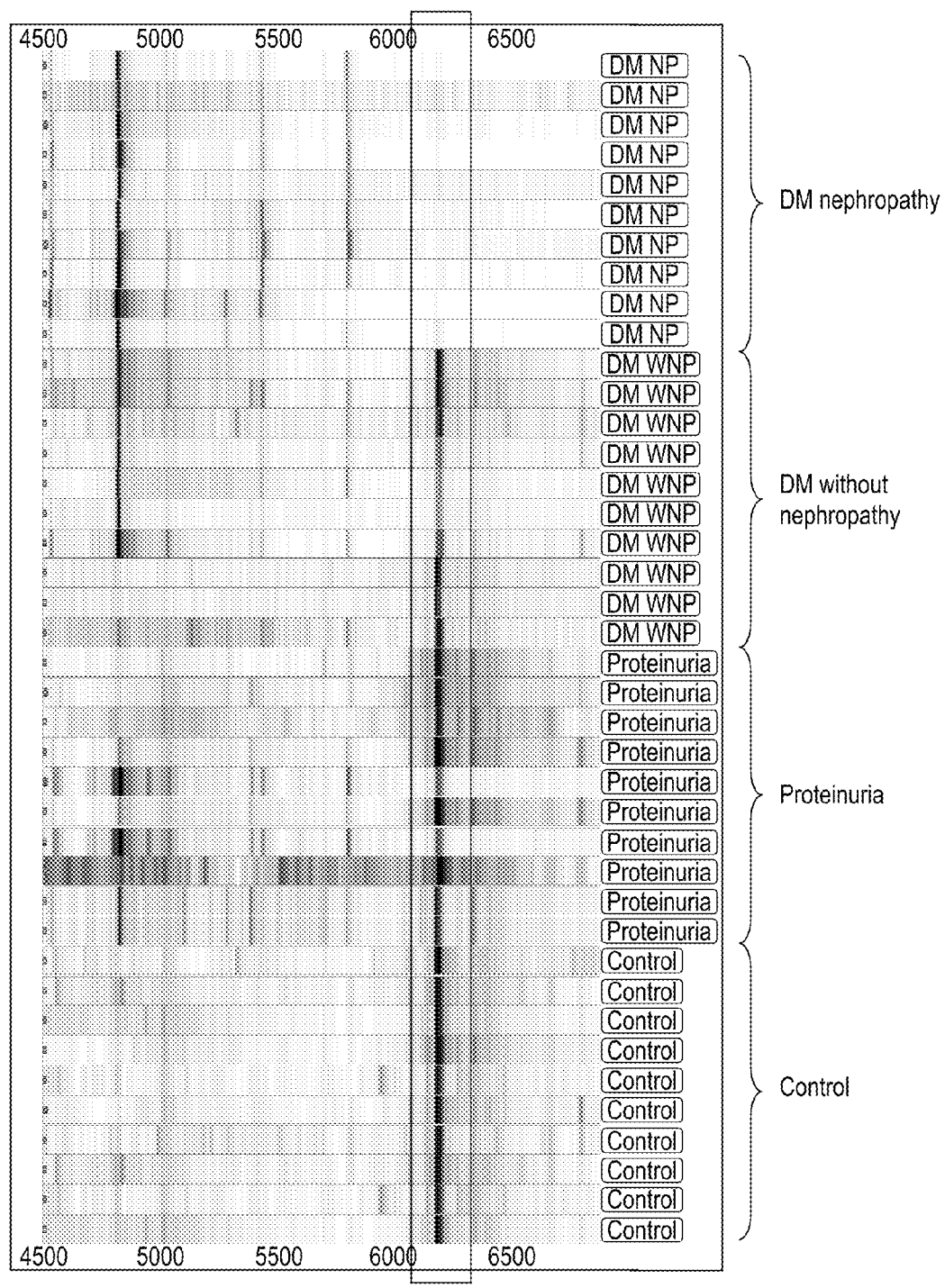
Figure 1A (Part 1)

Figure 1A (Part 2)
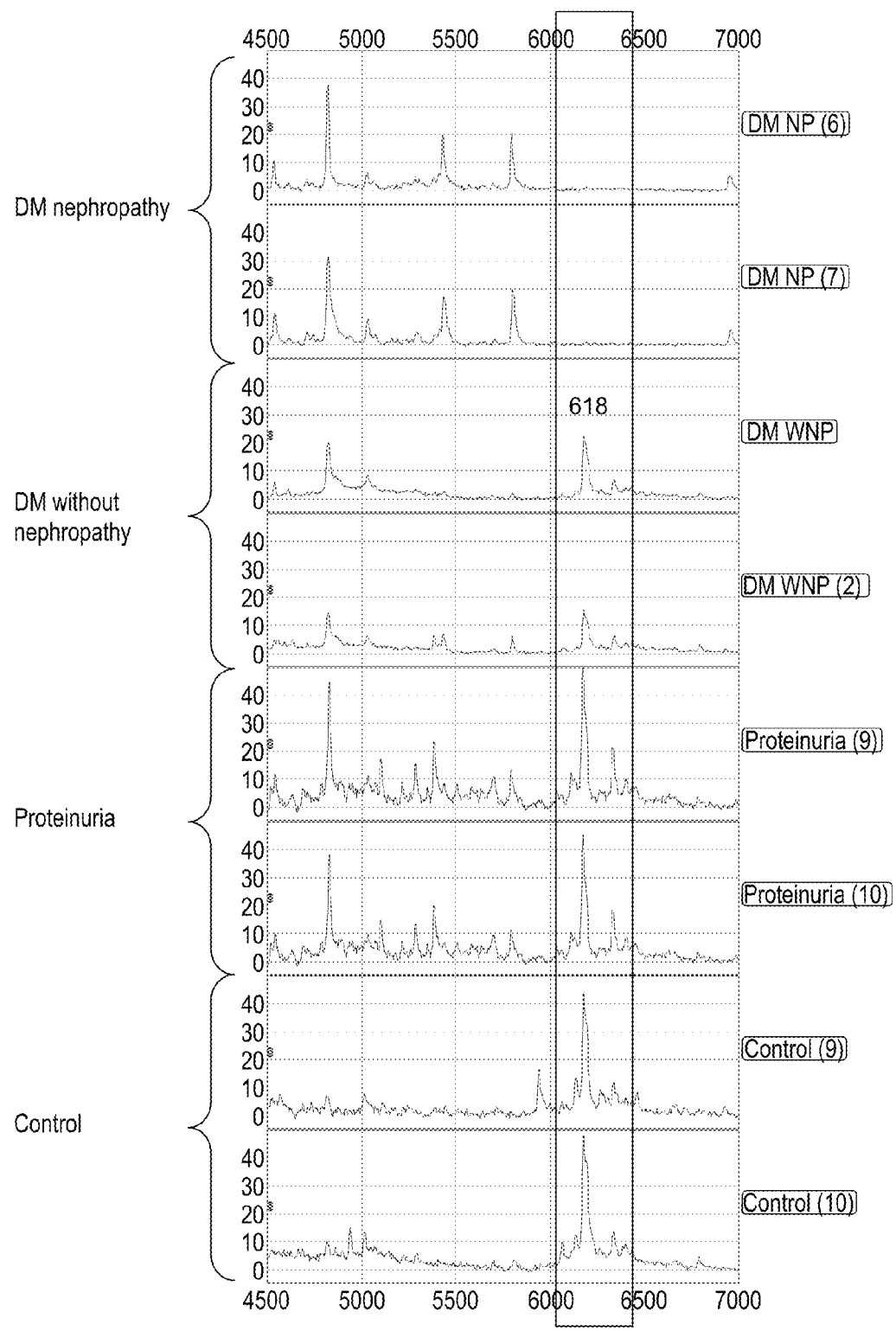

Tree with best p value markers

SEQUENCE LISTING

<160> NUMBER OF SEQ ID NOS: 14

<210> SEQ ID NO 1
<211> LENGTH: 128

```
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Ile Glu Pro
65                  70                  75                  80

Ser Leu Arg Gln Leu Ala Gln Lys Tyr Asn Cys Asp Lys Met Ile Cys
                85                  90                  95

Arg Lys Cys Tyr Ala Arg Leu His Pro Arg Ala Val Asn Cys Arg Lys
            100                 105                 110

Lys Lys Cys Gly His Thr Asn Asn Leu Arg Pro Lys Lys Val Lys
        115                 120                 125

<210> SEQ ID NO 2
<211> LENGTH: 119
<212> TYPE: PRT
<213> ORGANISM: Homo sapiens

<400> SEQUENCE: 2

Met Ser Arg Ser Val Ala Leu Ala Val Leu Ala Leu Leu Ser Leu Ser
1               5                   10                  15

Gly Leu Glu Gly Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Gln Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 3
<211> LENGTH: 52
<212> TYPE: PRT
<213> ORGANISM: Homo sapiens

<400> SEQUENCE: 3

Thr Ile Thr Leu Glu Val Glu Pro Ser Asp Thr Ile Glu Asn Val Lys
1               5                   10                  15

Ala Lys Ile Gln Asp Lys Glu Gly Ile Pro Pro Asp Gln Gln Arg Leu
            20                  25                  30

Ile Phe Ala Gly Lys Gln Leu Glu Asp Gly Arg Thr Leu Ser Asp Tyr
        35                  40                  45

Asn Ile Gln Lys
    50
```

<210> SEQ ID NO 4
<211> LENGTH: 76
<212> TYPE: PRT
<213> ORGANISM: Homo sapiens

<400> SEQUENCE: 4

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 5
<211> LENGTH: 16
<212> TYPE: PRT
<213> ORGANISM: Artificial Sequence
<220> FEATURE:
<223> OTHER INFORMATION: sequenced peptide

<400> SEQUENCE: 5

Thr Ile Thr Leu Glu Val Glu Pro Ser Asp Thr Ile Glu Asn Val Lys
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: sequenced peptide

<400> SEQUENCE: 6

Ile Gln Asp Lys Glu Gly Ile Pro Pro Asp Gln Gln Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: sequenced peptide

<400> SEQUENCE: 7

Glu Gly Ile Pro Pro Asp Gln Gln Arg
1               5

<210> SEQ ID NO 8
<211> LENGTH: 13
<212> TYPE: PRT
<213> ORGANISM: Artificial Sequence
<220> FEATURE:
<223> OTHER INFORMATION: sequenced peptide

<400> SEQUENCE: 8

Ile Glu Lys Val Glu His Ser Asp Leu Ser Phe Ser Lys
1               5                   10

<210> SEQ ID NO 9
<211> LENGTH: 10
<212> TYPE: PRT

```
<213> ORGANISM: Artificial Sequence
<220> FEATURE:
<223> OTHER INFORMATION: sequenced peptide

<400> SEQUENCE: 9

Val Glu His Ser Asp Leu Ser Phe Ser Lys
1               5                   10

<210> SEQ ID NO 10
<211> LENGTH: 17
<212> TYPE: PRT
<213> ORGANISM: Artificial Sequence
<220> FEATURE:
<223> OTHER INFORMATION: sequenced peptide

<400> SEQUENCE: 10

Asp Trp Ser Phe Tyr Leu Leu Tyr Tyr Thr Glu Phe Thr Pro Thr Glu
1               5                   10                  15

Lys

<210> SEQ ID NO 11
<211> LENGTH: 10
<212> TYPE: PRT
<213> ORGANISM: Artificial Sequence
<220> FEATURE:
<223> OTHER INFORMATION: sequenced peptide

<400> SEQUENCE: 11

Val Asn His Val Thr Leu Ser Gln Pro Lys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: sequenced peptide

<400> SEQUENCE: 12

Thr Leu Ser Asp Tyr Asn Ile Gln Lys
1               5

<210> SEQ ID NO 13
<211> LENGTH: 9
<212> TYPE: PRT
<213> ORGANISM: Artificial Sequence
<220> FEATURE:
<223> OTHER INFORMATION: sequenced peptide

<400> SEQUENCE: 13

Glu Ser Thr Leu His Leu Val Leu Arg
1               5

<210> SEQ ID NO 14
<211> LENGTH: 18
<212> TYPE: PRT
<213> ORGANISM: Artificial Sequence
<220> FEATURE:
<223> OTHER INFORMATION: sequenced peptide

<400> SEQUENCE: 14

Thr Ile Thr Leu Glu Val Glu Pro Ser Asp Thr Ile Glu Asn Val Lys
1               5                   10                  15

Ala Lys
```

BIOMARKERS FOR RENAL DISEASE

CROSS-REFERENCE TO RELATED APPLICATIONS

This application claims the benefit under 35 U.S.C. §119 (e) of U.S. Provisional Application No. 61/135,233 entitled "BIOMARKERS FOR RENAL DISEASE," filed on Jul. 17, 2008, which is incorporated herein by reference in its entirety.

BACKGROUND OF THE INVENTION

1. Field of the Invention

The invention relates to biomarkers for diagnosing renal diseases or for predicting the risk of a patient for developing a renal disease. More specifically, the invention provides ubiquitin fragment having a m/z of 6188, ubiquitin ribosomal fusion protein UbA52, and beta-2-microglobulin for methods of diagnosing or predicting renal diseases.

2. Background of the Invention

The number of patients with end stage renal disease is increasing at an enormous rate worldwide. This is mainly due to the rapidly increasing number of patients with diabetic nephropathy. Diabetes is, after arterial hypertension, the second most common disease in industrialized countries. According to the ADA ("American Diabetes Association")-criteria, the incidence is estimated to be around 8.5-9 percent. Incidence and prevalence, particularly of type 2 diabetes, have increased with an unproportional increase in prevalence. This is mainly due to reduced cardiovascular mortality in type 2 diabetics. Thus, a higher percentage of diabetics live long enough to develop other complications of the disease, including retinopathy and nephropathy. Whereas the incidence of nephropathy in type-1 diabetics is between 20 und 40 percent after a disease duration of 15-30 years, 10-50 percent of type 2-diabetics will develop renal involvement. Diabetic patients with renal disease have a poor prognosis. Compared to non-diabetics on dialysis, diabetics have a 22 percent increased first-year mortality and a 15 percent elevated 5-year mortality. Estimated costs for a diabetic dialysis patient are approximately 51,000 US $ per year compared to 39,000 US $ for non-diabetics. Risk factors for the development of diabetic nephropathy include genetic predisposition, poor glycemic control, arterial hypertension, and smoking.

At present, the definite diagnosis of nephropathy, such as diabetic nephropathy, is based on findings in renal biopsy. However, in most cases, the diagnosis can be reliably made in patients with macroalbuminuria in the presence of diabetic retinopathy. Microalbuminuria occurs when the kidney leaks small amounts of albumin into the urine. In a properly functioning body, albumin is not normally present in urine, because it is filtered from the bloodstream by the kidneys. In type 1 diabetics, microalbuminuria is the best predictor of subsequent development of nephropathy (defined as persistent macroalbuminuria (>300 mg/24 h)), with approximately 50 per cent of patients with microalbuminaria progressing to overt nephropathy. Conversely, microalbuminuria is of lesser value in type 2 diabetics, since these patients are older, with microalbuminuria often being induced by a variety of causes, including arterial hypertension or heart failure (Mykkanen L, et al., 1994). Thus, the predictive value of microalbuminuria is less strict.

Concerning diabetic nephropathy, proteomics have recently been applied with success to analyse kidney tissues from rodent models (Thongboonkerd V, et al (2004); Thongboonkerd V, et al. (2005)), but the larger amounts of material needed is a limiting factor for applications in human biopsies (Susztak K, et al. (2006)). The non-invasive and easy sampling of urine makes it attractive for proteomic analyses. Urinary proteomics were already applied to study type 2 diabetes and diabetic nephropathy (Hong C Y, et al. (2003); Rossing K, et al. (2005)).

Thus, in order to identify patients at risk for developing renal disease such as diabetic nephropathy, and in order to reliably diagnose renal diseases, additional markers are urgently needed.

Muller G A et al. (2007) generally describe the use of various techniques for proteomic analysis that can be used for monitoring renal disease-related protein changes, which may be useful for diagnostic tests.

Dihazi et al., Nephrology (2005a), describe the identification of biomarkers indicative of nephropathy in urine by way of mass spectrometry. The report mentions the m/z ratios of various prospective proteins found, but only identifies one of these proteins further.

Sun L et al., JBC (2002) describe the up-regulation of the mouse UbA52 gene in kidney tissue of newborn diabetic mice. The report speculates that UbA52 might be relevant to the pathobiology of diabetic nephropathy. In the kidney, the UbA52 was exclusively located in renal tubules, and its expression in mice kidney was found to be proportional to the glucose levels in blood. Gene expression analyses displayed an over-expression of the UbA52 protein in kidney of diabetic newborn mice.

Further, Schardijn and Statius showed a strong correlation between the $\beta$2-M level in serum and the glomerular filtration rate (Schardijn G, et al. (1979); Schardijn G H, et al., (1987)). Alteration in $\beta$2-M level has been observed in patients with different diseases, including diabetic nephropathy (Schaub S, et al. (2005); ); Schardijn G H, et al., (1987); Hong C Y, et al. (1998)).

SUMMARY OF THE INVENTION

Accordingly, in certain embodiments, the present invention relates to a method for diagnosing a renal disease in a patient, comprising determining the level of a ubiquitin fragment having a m/z of 6188, or the level of a nucleic acid encoding a ubiquitin fragment having a m/z of 6188, as defined in the claims. Also, in other related embodiments, the present invention relates to a method for diagnosing a renal disease in a patient, comprising determining the level of ubiquitin ribosomal fusion protein UbA52, or the level of a nucleic acid encoding UbA52, as defined in the claims. In further embodiments, the invention relates to a method for predicting the risk of a patient for developing a renal disease, comprising determining the level of a ubiquitin fragment having a m/z of 6188 or ubiquitin ribosomal fusion protein UbA52, or their respective nucleic acids, as defined in the claims. The methods of the invention may further comprise determining the level of a ubiquitin fragment having a m/z of 6188; or determining the level of UbA52; or determining the level of beta-2-microglobulin, or their respective nucleic acids, as defined in the claims. Finally, the invention provides a kit for diagnosing a renal disease or for predicting the risk for a patient of developing a renal disease, as defined in the claims. In addition, the invention provides a method for diagnosing a renal disease or for predicting the risk of a patient for developing a renal disease by determining the presence of a ubiquitin-degrading activity and a kit for use in this method, as defined in the claims.

DESCRIPTION OF THE FIGURES

FIG. 3. Workflow of protein fractionation and purification of the protein markers. The purification and identification of the m/z 6188 is given as example. (A), SDS gel from the anionic exchange fractionation. F1-5 indicates the different pH fractions eluted from the column. (B), SDS gel from the reverse phase fractionation. F4 from the anionic exchange fractionation containing the highest amount of the mass peak m/z 6188 was taken for the fractionation. The elutes from the different ACN concentrations are showing on the SDS gel. The fraction from the 20% ACN shows the highest purity of the protein m/z 6188. ACN: acetonitrile; FT: Flow through.

DETAILED DESCRIPTION OF THE INVENTION

Figure 1B:
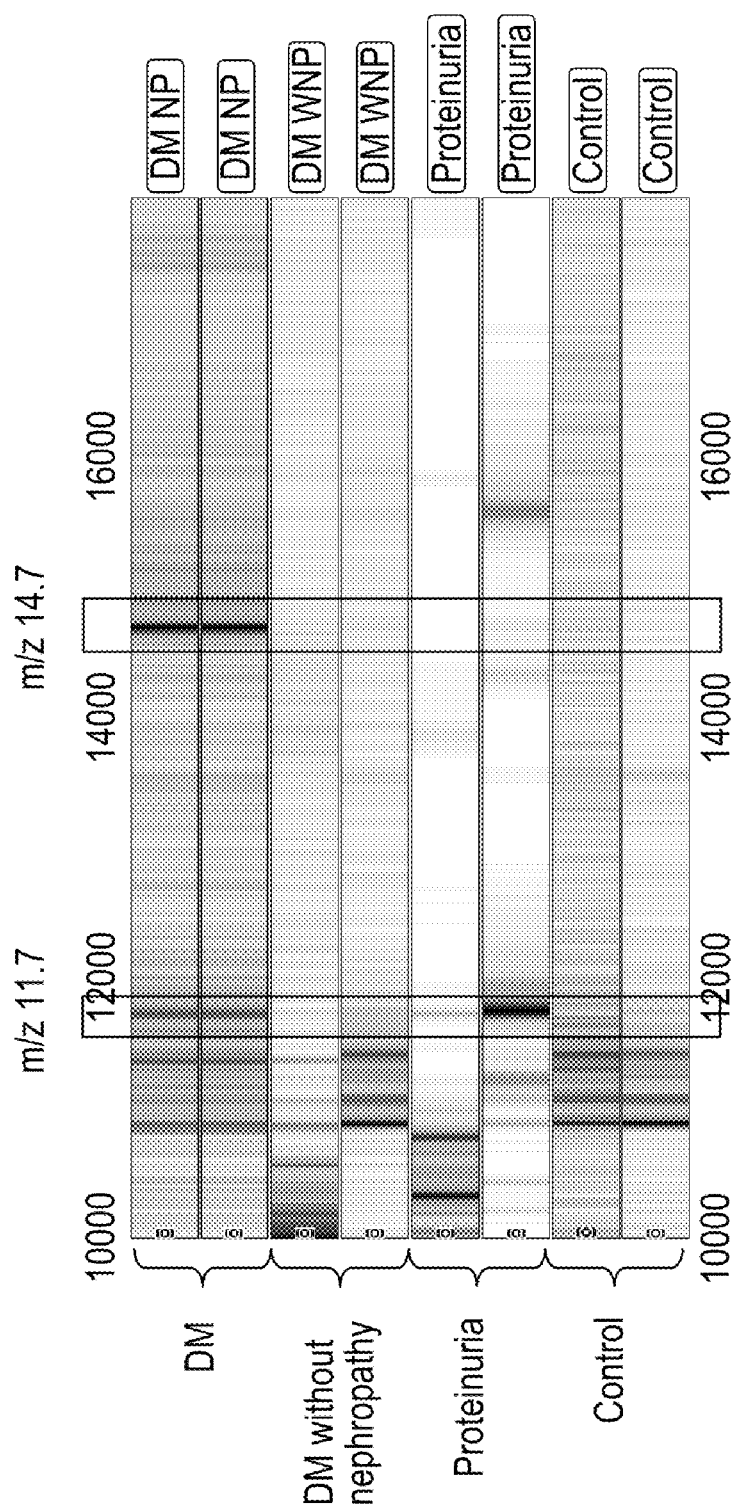
FIG. 1. Representative SELDI-TOF MS protein pattern from urine of the different investigated groups. (A), the low molecular weight range between 4500 and 7000 Da in 10 urine samples from each studied group (10 from DM-NP, 10 from DM-WNP, 10 from patients with proteinuria, and 10 from healthy control) illustrated in gel view in left panel. The mass peak with m/z 6188 discriminating DM-NP from the other groups is highlighted with the box. The right panel indicates the mass spectral view from the same mass peak. (B), gel view from the middle molecular weight range 10,000-18,000. Boxes indicate the peak masses m/z 11774 and m/z 14766 found to be differentially excreted in DM-NP patient urines.

The present inventors have found that, surprisingly, certain proteins derived from the sample of a patient can be used in methods for diagnosing renal diseases or predicting the risk of a patient for developing a renal disease, by determining the level of one or more of the polypeptides of the invention, or the level of one or more nucleic acids encoding the polypeptides of the invention, alone or in combination with other markers for renal disease.

Accordingly, the present invention provides methods for diagnosing a renal disease in a patient, e.g., diabetic nephropathy, or identifying a patient at risk of developing a renal disease, e.g., diabetic nephropathy, comprising determining the levels of one or more polypeptides of the present invention in a biological sample obtained from a patient. In addition, the present invention provides methods for diagnosing a renal disease in a patient, e.g., diabetic nephropathy, or identifying a patient at risk of developing a renal disease, e.g., diabetic nephropathy, comprising determining the levels of one or more polynucleotides encoding polypeptides of the present invention in a biological sample obtained from a patient. Additionally, the present invention provides methods for diagnosing a renal disease in a patient, e.g., diabetic nephropathy, or identifying a patient at risk of developing a renal disease, e.g., diabetic nephropathy, comprising determining the levels of antibodies specific for one or more polypeptides of the present invention in a biological sample obtained from a patient. In addition, the present invention provides related compositions and kits useful for practicing the methods of the invention.

Thus, in a first aspect, the present invention relates to a method for diagnosing a renal disease in a patient, comprising determining the level of a ubiquitin fragment having a mass-to-charge ratio (m/z) of 6188 (ubiquitin m/z 6188), or the level of a nucleic acid encoding ubiquitin m/z 6188, in a sample derived from said patient, wherein the substantial absence of ubiquitin m/z 6188 or the nucleic acid encoding ubiquitin m/z 6188 compared to a control is indicative of the renal disease in said patient. In related embodiments, a reduced level of ubiquitin m/z 6188 or a nucleic acid encoding ubiquitin m/z 6188 is indicative of the renal disease in said patient. In particular embodiments, the level of ubiquitin m/z 6188 is reduced to less than 50%, less than 25%, less than 20%, less than 15%, less than 10%, less than 5%, less than 2%, less than 1%, or less than 0.5% the level in a control sample.

In a second aspect, the present invention relates to a method for predicting the risk of a patient for developing a renal disease, comprising determining the level of ubiquitin m/z 6188, or the level of a nucleic acid encoding ubiquitin m/z 6188, in a sample derived from said patient, wherein the substantial absence of ubiquitin m/z 6188 or the nucleic acid encoding ubiquitin m/z 6188 compared to a control is indicative of a risk for the patient of developing the renal disease. In related embodiments, a reduced level of ubiquitin m/z 6188 or a nucleic acid encoding ubiquitin m/z 6188 is indicative of a risk for the patient of developing the renal disease. In particular embodiments, the level of ubiquitin m/z 6188 is reduced to less than 50%, less than 25%, less than 20%, less than 15%, less than 10%, less than 5%, less than 2%, less than 1%, or less than 0.5% the level in a control sample.

In certain embodiment, the methods of the invention further comprise (i) determining the level of beta-2-microglobulin (SEQ ID NO: 2), or the level of a nucleic acid encoding beta-2-microglobulin, compared to a control; or (ii) determining the level of ubiquitin ribosomal fusion protein UbA52 (SEQ ID NO: 1), or the level of a nucleic acid encoding UbA52, compared to a control; or (iii) determining the level of both beta-2-microglobulin and UbA52, or the level of both a nucleic acid encoding beta-2-microglobulin and a nucleic acid encoding UbA52, compared to a control; wherein an elevated level of beta-2-microglobulin and/or UbA52, or an elevated level of a nucleic acid encoding beta-2-microglobulin and/or a nucleic acid encoding UbA52, is indicative of the renal disease in said patient or is indicative of a risk for the patient of developing the renal disease. In particular embodiments, the level of beta-2-microglobulin and/or UbA52, or the level of a nucleic acid encoding beta-2-microglobulin and/or UbA52, is elevated to at least two-fold, at least five-fold, or at least ten-fold the level in a control sample. Generally, it is contemplated that the level of one or more further markers for renal disease or other markers of interest are determined in the sample.

Furthermore, in another aspect, the present invention relates to a method for diagnosing a renal disease in a patient, comprising determining the level of ubiquitin ribosomal fusion protein UbA52 (SEQ ID NO: 1), or the level of a nucleic acid encoding UbA52, in a sample derived from said patient, wherein an elevated level of UbA52 or the nucleic acid encoding UbA52 compared to a control is indicative of the renal disease in said patient. In particular embodiments, the level of UbA52, or the level of a nucleic acid encoding UbA52, is elevated to at least two-fold, at least five-fold, or at least ten-fold the level in a control sample.

In another aspect, the present invention provides a method for predicting the risk of a patient for developing a renal disease, comprising determining the level of ubiquitin ribosomal fusion protein UbA52, or the level of a nucleic acid encoding UbA52, in a sample derived from said patient, wherein an elevated level of UbA52 or the nucleic acid encoding UbA52 compared to a control is indicative of the renal disease in said patient. In particular embodiments, the level of UbA52, or the level of a nucleic acid encoding UbA52, is elevated to at least two-fold, at least five-fold, or at least ten-fold the level in a control sample.

In particular embodiments, the methods of the invention further comprise (i) determining the level of ubiquitin m/z 6188, or the level of a nucleic acid encoding m/z 6188, compared to a control; or (ii) determining the level of beta-2-microglobulin (SEQ ID NO: 2), or the level of a nucleic acid encoding beta-2-microglobulin, compared to a control; or (iii) determining the level of both ubiquitin m/z 6188 and beta-2-microglobulin, or of both a nucleic acid encoding ubiquitin m/z 6188 and a nucleic acid encoding beta-2-microglobulin, compared to a control; wherein the substantial absence or a reduced level of ubiquitin m/z 6188 and/or an elevated level of beta-2-microglobulin, or a nucleic acid encoding ubiquitin m/z 6188 and/or a nucleic acid encoding beta-2-microglobulin, is indicative of the renal disease in said patient or is indicative of a risk for the patient of developing the renal disease. Generally, it is contemplated that the level of one or more further markers for renal disease or other markers of interest are determined in the sample. In particular embodiments, the level of ubiquitin m/z 6188 is reduced to less than 50%, less than 25%, less than 20%, less than 15%, less than 10%, less than 5%, less than 2%, less than 1%, or less than 0.5% the level in a control sample. In particular embodiments, the level of beta-2-microglobulin, or the level of a nucleic acid encoding beta-2-microglobulin, is elevated to at least two-fold, at least five-fold, or at least ten-fold as compared to the level in a control sample.

In yet another aspect, the present invention provides a method for diagnosing a renal disease in a patient or a method for predicting the risk of a patient for developing a renal disease, comprising determining the level of beta-2-microglobulin (SEQ ID NO: 2) or of a nucleic acid encoding beta-2-microglobulin in a sample derived from said patient, wherein an elevated level of beta-2-microglobulin or the nucleic acid compared to a control is indicative of a renal disease in said patient. In particular embodiments, the level of beta-2-microglobulin, or the level of a nucleic acid encoding beta-2-microglobulin, is elevated to at least two-fold, at least five-fold, or at least ten-fold as compared to the level in a control sample.

In particular embodiments, the methods of the invention may comprise: determining the level of ubiquitin m/z 6188 or a nucleic acid encoding ubiquitin m/z 6188; determining the level of ubiquitin m/z 6188 or a nucleic acid encoding ubiquitin m/z 6188 in combination with the level of beta-2-microglobulin or a nucleic acid encoding beta-2-microglobulin; determining the level of ubiquitin m/z 6188 or a nucleic acid encoding ubiquitin m/z 6188 in combination with the level of UbA52 or a nucleic acid encoding UbA52; or determining the level of ubiquitin m/z 6188 or a nucleic acid encoding ubiquitin m/z 6188 in combination with both the level of beta-2-microglobulin or a nucleic acid encoding beta-2-microglobulin and the level of UbA52 or a nucleic acid encoding UbA52. In general, a reduced level of ubiquitin m/z 6188, alone or in combination with an increased level of beta-2-microglobulin and/or UbA52 is indicative of a renal disease or increased risk of developing a renal disease, such as diabetic nephropathy.

In a further aspect, the present invention includes a method for diagnosing a renal disease in a patient or a method for predicting the risk of a patient for developing a renal disease, comprising determining the level of ubiquitin-degrading activity in a biological sample obtained from a patient, wherein a reduced level of ubiquitin-degrading activity in the sample as compared to a control is indicative of the renal disease or a risk for the patient in developing the renal disease. In one embodiment, the level of ubiquitin-degrading activity in a sample is determined by adding exogenous ubiquitin to the sample under suitable conditions known in the art, and determining the formation of ubiquitin m/z 6188 in the sample, which formation is indicative of a ubiquitin-degrading activity in the sample.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. All publications, patents and patent applications cited herein, whether supra or infra, are hereby incorporated by reference in their entirety.

A "renal disease" as used herein is preferably nephropathy, which is characterized by renal tissue damages and kidney dysfunction. Preferably, the renal disease is diabetic nephropathy and/or tubular nephropathy. Diabetic nephropathy is characterized by a spectrum of progressive renal lesions secondary to diabetes mellitus, ranging from renal hyperfiltration to end stage kidney disease. Diabetic nephropathy is characterized by glomerular damage leading to the appearance of microalbuminurea. Albumin excretion rates can exceed 200 micrograms/minute, and blood levels of creatinine and urea-nitrogen rise. GFR decreases to less than 75 ml/min, large amounts of protein pass into the urine, and high blood pressure almost always occurs. Levels of creatinine and urea-nitrogen in the blood rise. On the other hand, tubular nephropathy is characterized by tubular injury and excretion of low molecular weight proteins.

A "patient" as used herein preferably refers to a human patient; but it may also include a mammal such as a mouse, monkey, rat, rabbit, guinea pig, dog, or cat.

"Determining the level" of any of the polypeptides and/or proteins of the invention can be effected by various techniques known in the art. In certain embodiments, the level or the amount of any polypeptide or protein of interest in a sample can be determined by mass spectrometry, such as the well-known MALDI-TOF technique, or ESI-MS-MS. The mass spectrometry can be coupled to a prior separation step of the polypeptides or proteins on a protein chip, such as a SELDI protein chip, an example of which is the SAX2 protein array described in the examples herein. Also, mass spectrometry methods can be coupled to a prior separation step of the polypeptides or proteins by means of capillary electrophoresis; the analysis of the separated protein material can then be effected by subsequent electrospray TOF-MS. Also, liquid chromatography methods coupled to mass spectrometry (LC-MS) are known in the art and suitable for the methods of the invention. Typically, the level of a specific polypeptide or protein can be determined by measuring peak intensities of the respective polypeptide or protein in a mass spectrum (the mass-to-charge ratios of the respective polypeptide/protein species). These peak intensities can be compared e.g. to the corresponding peak intensities in a mass spectrum obtained from a sample or samples from a control or control group of patients, as defined herein. Advantageously, a series of mass spectra derived from control samples that have been treated in the same way as the sample of interest are obtained, and normalized with the help of a computer program that is typically included in the setup of a mass spectrometer. Then, the peak intensities of the mass peaks of interest may be compared to the peak intensities in a normalized peak profile of the control group. The relative intensity of the peaks of interest in the test sample and the control can be translated into a level or amount of polypeptide or protein that is present in a sample of interest. Examples for techniques for obtaining samples from a patient of interest and a control group, and determining the protein profiles contained in these samples, are described e.g. in the examples herein.

Thus, in the methods of the invention, the term "an elevated level" of any of the polypeptides or proteins of the invention or of the nucleic acids of the invention refers to a level or amount of the polypeptide/protein or nucleic acid in the investigated sample that is elevated when compared to a control. For example, if the m/z peak observed in a mass spectrum for one or more of the polypeptides or proteins of the invention has a larger intensity than the corresponding normalized peak observed in the sample of the control group, the respective polypeptide or protein is present at an elevated level. In various embodiments, an elevated level indicates a level at least 1.5-fold, at least two-fold, at least three-fold, at least five-fold, or at least ten-fold, the level in a control sample.

Analogously, the term "a reduced level" of any of the polypeptides or proteins of the invention or of the nucleic acids of the invention refers to a level or amount of the polypeptide/protein or nucleic acid in the investigated sample that is reduced when compared to a control. For example, if the m/z peak observed in a mass spectrum for one or more of the polypeptides or proteins of the invention has a smaller intensity than the corresponding normalized peak observed in the sample of the control group, the respective polypeptide or protein is present at a reduced level. In various embodiments, a reduced level indicates a level less than 75%, less than 50%, less than 25%, less than 20%, less than 15%, less than 10%, less than 5%, less than 2%, less than 1%, or less than 0.5% the level in a control sample.

The term "substantial absence" of a polypeptide, a protein, or a nucleic acid in a sample according to the invention refers to complete absence of the polypeptide, a protein, or a nucleic acid from a sample, or to an almost complete absence, e.g. as determined by the quantitative techniques described herein. Typically, if a polypeptide or protein of interest of the invention is absent or substantially absent from a sample, the m/z peak of the corresponding molecule is absent (i.e. zero %) from the mass spectrum when compared to the corresponding m/z peak in normalized spectra of samples from a control group, or is merely present in an amount of 0.1%, 0.2%, 0.3%, 0.4%, 0.5%, 1%, 2 %, 3%, 4%, 5%, 6%, 7%, 8%, 9% or 10% of the corresponding peak in a control group.

Suitable controls include e.g. samples from healthy patients, e.g. patients that do not show signs of any renal disease, which samples have been treated in exactly the same manner as the sample of the patient of interest. Suitable controls could also be derived from patient groups that show signs of disease other than the specific renal disease that is to be tested in the methods of the invention. For example, if the renal disease that is to be diagnosed, or of which the risk is to be predicted, is diabetic nephropathy, suitable controls can be derived e.g. from patients or patient groups comprising healthy non-diabetic patients, patients showing proteinuria due to non-diabetic disease, or diabetic patients without any symptoms of nephropathy and/or microalbuminuria.

Further preferred methods suitable for determining the level of a polypeptide or protein in a given sample are e.g. antibody-based techniques. Examples for such techniques are ELISA assays or Western blots, which are well known in the art. Such techniques allow the quantification of the levels or the amounts of polypeptides or proteins in a variety of samples.

There are a variety of assay formats known to those of ordinary skill in the art for using a binding agent to detect polypeptide markers of renal disease in a sample, and any of these may be used to practice the methods of the invention. In general, the level of a marker of renal disease of the present invention in a patient may be determined by (a) contacting a biological sample obtained from a patient with a binding agent; (b) detecting in the sample a level of polypeptide that binds to the binding agent; and (c) comparing the level of polypeptide with a predetermined cut-off value or control value.

In one embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length polypeptides such as ubiquitin m/z6188, beta-2-microglobulin, and UbA52, as well as polypeptide portions thereof to which the binding agent binds, as described above.

The solid support may be any material known to those of ordinary skill in the art to which the polypeptide marker may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with or at risk of a renal disease. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Reporter groups that may be used include, e.g., radionuclides, enzymes, fluorescent, chemiluminescent, or chromogenic agents as well as substrates, cofactors, inhibitors, magnetic particles, and the like.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a renal disease or risk for developing a renal disease, such as diabetic nephropathy, the signal detected from the reporter group that remains bound to the solid support is generally compared to a signal that corresponds to a predetermined cut-off value or control value. In one preferred embodiment, the cut-off value for the detection of a renal disease is the average mean signal obtained when the immobilized antibody is incubated with samples from patients without the renal disease. In general, a sample generating a signal that is three standard deviations above the predetermined cut-off value is considered positive for the renal disease or risk thereof. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a renal disease or risk thereof.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a renal disease or risk thereof. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the renal disease markers or binding agents of the present invention. The above descriptions are intended to be exemplary only. For example, it will be apparent to those of ordinary skill in the art that the above protocols may be readily modified to use polypeptides to detect antibodies that bind to such polypeptides in a biological sample. The detection of such specific antibodies may correlate with the presence or risk for a renal disease.

The nucleic acids of the invention include RNA, mRNA, dsRNA, DNA, ssDNA, and dsDNA. Preferably, the methods of the invention involve the determination of the level of RNA molecules according to the invention, such as mRNA encoding the polypeptides of the invention. The level of RNA in a sample can be determined e.g. by techniques of RNA extraction e.g. by commercially available kits, and by subsequent quantitative PCR techniques, such as RT-PCR, which are known in the art. For example one or more oligonucleotide probes that specifically hybridize to a polynucleotide encoding a protein of the present invention may be used in a hybridization assay to detect the presence of polynucleotides encoding one or more of the proteins described herein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art.

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a renal disease. The amplification reaction may be performed on several dilutions of cDNA spanning two orders of magnitude. A two-fold or greater increase in expression in several dilutions of the test patient sample as compared to the same dilutions of the control sample is typically considered positive.

The samples of the present invention are derived from a patient of interest, and include, e.g., urine sample, a biopsy, such as a kidney tissue sample or a kidney tissue biopsy, a saliva sample, or a blood sample. Preferably, the sample is a urine sample, which offers the advantage of being readily obtainable by non-invasive procedure, and in large amounts. Nevertheless, it is also contemplated that a sample derived from a patient according to the invention may be derived from another body fluid such as serum, or saliva, or it may be a tissue sample, such as a kidney tissue sample or a kidney tissue biopsy. Methods for obtaining such samples from a patient are known to the skilled person.

The patient of interest that is to be examined in the methods of the invention includes, but is not limited to, a diabetic patient, a diabetic patient showing symptoms of nephropathy, a diabetic patient without symptoms of nephropathy and/or microalbuminuria, a patient showing proteinuria due to non-diabetic disease, or a patient showing no symptoms of diabetes or renal disease. Preferably, the patient of interest to be examined by way of the methods of the invention is a diabetic patient. In particular embodiments, a patient is diagnosed with or considered at risk of developing type 1 or type 2 diabetes.

"Predicting the risk" of a patient for developing a renal disease as used herein includes giving a prognosis whether or not the patient in question has an elevated risk of developing a renal disease within a certain amount of time, or whether the patient has no elevated risk of developing a renal disease.

A "ubiquitin fragment having a mass-to-charge ratio (m/z) of 6188" is characterized by its m/z value of 6188, as determined e.g. by MALDI-TOF mass spectrometry. Preferably, a ubiquitin fragment having a mass-to-charge ratio (m/z) of 6188 according to the invention comprises the amino acid sequence shown in SEQ ID NO: 3, preferably consists of the amino acid sequence shown in SEQ ID NO: 3. However, it is also contemplated that ubiquitin m/z 6188 comprises more amino acid residues than shown in SEQ ID NO: 3, preferably additional amino acid residues at the N-terminus or C-terminus that also occur in the naturally occurring form of human ubiquitin, as shown in SEQ ID NO: 4. In addition, it is also contemplated that ubiquitin m/z 6188 may comprise less amino acids than shown in SEQ ID NO: 3, i.e. truncated forms that lack a few amino acid residues either at the N-terminus or the C-terminus of the molecule or at both termini. Thus, ubiquitin m/z 6188 according to the invention may comprise 1, 2, 3, 4, 5, 6, 7, 8, 9, or 10 residues added either at the N-terminus or the C-terminus, or at both termini, or may lack 1, 2, 3, 4, 5, 6, 7, 8, 9, or 10 residues added either at the N-terminus or the C-terminus, or at both termini.

A nucleic acid encoding a ubiquitin fragment having a mass-to-charge ratio (m/z) of 6188 can be a RNA, particularly an mRNA, or a DNA molecule comprising a nucleic acid sequence that encodes ubiquitin m/z 6188, for example the amino acid sequence shown in SEQ ID NO: 3. However, it is also contemplated that a nucleic acid encoding ubiquitin m/z 6188 encodes a nucleic acid sequence encoding a polypeptide comprising ubiquitin m/z 6188, for example forms of ubiquitin m/z 6188 comprising additional amino acid residues either at the N-terminus or the C-terminus, or at both termini as defined above, or lacking amino acid residues either at the N-terminus or the C-terminus, or at both termini as defined above.

The "ubiquitin ribosomal fusion protein UbA52" is an ubiquitin fusion protein (128 amino acid) made of 60S ribosomal protein (52 amino acid) attached to an ubiquitin peptide (76 amino acid). UbA52 as used herein preferably comprises a protein having the amino acid sequence of SEQ ID NO: 1, and preferably consists of a protein having the amino acid sequence of SEQ ID NO: 1. Preferably, if the patient to be examined is a human patient, the human isoform of UbA52 is determined in a sample of said patient. It is contemplated that truncated forms of UbA52 are also included in the term "UbA52" as used herein, i.e. an forms in which one ore more amino acids of SEQ ID NO: 1 are missing. Thus, UbA52 according to the invention may lack 1, 2, 3, 4, 5, 6, 7, 8, 9, or 10 residues added either at the N-terminus or the C-terminus, or at both termini, of SEQ ID NO:1.

A nucleic acid encoding a UbA52 polypeptide can be a RNA, particularly an mRNA, or a DNA molecule comprising a nucleic acid sequence that encodes UbA52, for example the amino acid sequence shown in SEQ ID NO. 1. However, it is also contemplated that a nucleic acid encoding UbA52 encodes a nucleic acid sequence encoding a polypeptide comprising UbA52, for example forms of UbA52 lacking amino acid residues either at the N-terminus or the C-terminus, or at both termini, as defined above.

"Beta-2-microglobulin" as used herein preferably refers to a polypeptide comprising an amino acid sequence as shown in SEQ ID NO: 2, preferably consists of SEQ ID NO:2. It is also contemplated that forms of beta-2-microglobulin are comprised in the term that lack a few amino acid residues either at the N-terminus or the C-terminus of the protein, or at both termini. For example, a beta-2-microglobulin according to the invention may also lack 1, 2, 3, 4, 5, 6, 7, 8, 9, or 10 amino acid residues either at the N-terminus or the C-terminus of SEQ ID NO: 2, or at both termini.

A nucleic acid encoding a beta-2-microglobulin polypeptide can be a RNA, particularly an mRNA, or a DNA molecule comprising a nucleic acid sequence that encodes beta-2-microglobulin, for example the amino acid sequence shown in SEQ ID NO. 2. However, it is also contemplated that a nucleic acid encoding beta-2-microglobulin encodes a nucleic acid sequence encoding a polypeptide comprising beta-2-microglobulin, for example forms of beta-2-microglobulin lacking amino acid residues either at the N-terminus or the C-terminus, or at both termini, as defined above.

In a further preferred embodiment, the methods of the invention further comprise determining the ratio of the level of ubiquitin m/z 6188 to the level of UbA52, or the ratio of the level of a nucleic acid encoding ubiquitin m/z 6188 to the level of a nucleic acid encoding UbA52, wherein a ratio of less than 5 is indicative of the renal disease in said patient. In other related embodiments, a ratio of less than 4.5, less than 4, less than 3.5, less than 3, less than 2.5, less than 2, or less than 1.5 is considered indicative of the renal disease. This means that typically, a renal disease such as diabetic nephropathy is fully developed in a patient who presents himself with a ratio of the level of ubiquitin m/z 6188 to the level of UbA52 or their respective nucleic acids of less than 5.

In a further embodiment, the methods of the invention further comprise determining the ratio of the level of ubiquitin m/z 6188 to the level of UbA52, or the ratio of the level of a nucleic acid encoding ubiquitin m/z 6188 to the level of a nucleic acid encoding UbA52, wherein a ratio of less than 85 is indicative of a risk for the patient of developing the renal disease. In other related embodiments, a ratio of less than 80, less than 70, less than 60, less than 50, less than 40, less than 30, less than 20, less than 10, or less than 7 is considered is indicative of a risk for the patient of developing the renal disease. This means that typically, a renal disease such as diabetic nephropathy is beginning to develop or is in the first stages of development in a patient who presents himself with a ratio of the level of ubiquitin m/z 6188 to the level of UbA52 or their respective nucleic acids of less than 85.

In another preferred embodiment, the methods of the invention further comprise determining the ratio of the level of ubiquitin m/z 6188 to the level of beta-2-microglobulin, or the ratio of the level of a nucleic acid encoding ubiquitin m/z 6188 to the level of a nucleic acid encoding beta-2-microglobulin, wherein a ratio of less than 5 is indicative of the renal disease in said patient. In other related embodiments, a ratio of less than 4.5, less than 4, less than 3.5, less than 3, less than 2.5, less than 2, or less than 1.5 is considered indicative of the renal disease. This means that typically, a renal disease such as diabetic nephropathy is fully developed in a patient who presents himself with a ratio of the level of ubiquitin m/z 6188 to the level of beta-2-microglobulin or their respective nucleic acids of less than 5.

In further embodiment, the methods of the invention further comprise determining the ratio of the level of ubiquitin m/z 6188 to the level of beta-2-microglobulin, or the ratio of the level of a nucleic acid encoding ubiquitin m/z 6188 to the level of a nucleic acid encoding beta-2-microglobulin, wherein a ratio of less than 70 is indicative of the renal disease in said patient. In other related embodiments, a ratio of less than 65, less than 60, less than 50, less than 40, less than 30, less than 20, less than 10, or less than 7 is considered is indicative of a risk for the patient of developing the renal disease. This means that typically, a renal disease such as diabetic nephropathy is beginning to develop or is in the first stages of development in a patient who presents himself with a ratio of the level of ubiquitin m/z 6188 to the level of beta-2-microglobulin or their respective nucleic acids of less than 70.

As is described above and exemplified herein, determining the ratio of the level of one protein or polypeptide of interest to the level of another polypeptide or protein of interest includes, for example, determining the m/z peak intensity in a mass spectrum, preferably the normalized peak intensity obtained from the respective proteins, and forming a ratio using these values. However, it is also contemplated that the level of a polypeptide or protein of interest can be derived by other techniques, such as antibody-based techniques like ELISA or Western blotting. If the levels of nucleic acids are to be determined in a sample, well-known methods such as quantitative PCR can for example be used for the quantification of mRNA levels.

In another preferred embodiment, the methods of the invention further comprise determining the ratio of the level of ubiquitin m/z 6188 to the level of UbA52, or the ratio of the level of a nucleic acid encoding ubiquitin m/z 6188 to the level of a nucleic acid encoding UbA52, in a patient and a control group under identical conditions, wherein a ratio of less than 85 in the patient and a ratio of at least 85 in the control group is indicative of the renal disease in said patient or is indicative of a risk for the patient of developing the renal disease. In other related embodiments, a ratio of less than 80, less than 75, less than 70, less than 60, less than 50, less than 40, less than 30, less than 20, less than 10, less than 7, less than 5, less than 4, less than 3, or less than 2 in the patient, accompanied by a ratio of at least 85, at least 90, at least 95, at least 100, at least 110, or at least 120 in the control group, is considered indicative of the renal disease or risk thereof in the patient. In a particular embodiment, a ratio of less than 5 in the patient and of at least 85 in the control group, is considered indicative of the renal disease in the patient, i.e. typically, the renal disease such as diabetic nephropathy is present in the patient.

In yet another preferred embodiment, the methods of the invention further comprise determining the ratio of the level of ubiquitin m/z 6188 to the level of beta-2-microglobulin, or the ratio of the level of a nucleic acid encoding ubiquitin m/z 6188 to the level of a nucleic acid encoding beta-2-microglobulin, in a patient and a control group under identical conditions, wherein a ratio of less than 70 in the patient and a ratio of at least 70 in the control group is indicative of the renal disease in said patient or is indicative of a risk for the patient of developing the renal disease. In other related embodiments, a ratio of less than 65, less than 60, less than 55, less than 50, less than 45, less than 40, less than 30, less than 20, less than 10, less than 7, less than 5, less than 4, less than 3, or less than 2 in the patient, accompanied by a ratio of at least 70, at least 75, at least 80, at least 85, at least 90, at least 95, at least 100, at least 110, or at least 120 in the control group, is considered indicative of the renal disease or risk thereof in the patient. In a particular embodiment, a ratio of less than 5 in the patient and of at least 70 in the control group is considered indicative of the renal disease in the patient, i.e. typically, the renal disease such as diabetic nephropathy is present in the patient.

As defined above, suitable control groups can include, e.g., healthy non-diabetic patients, patients showing proteinuria due to non-diabetic disease, and diabetic patients without symptoms of nephropathy and/or microalbuminuria.

Determining the ratio of the level of one polypeptide or nucleic acid of the invention to the level of another polypeptide or nucleic acid of the invention, or their respective nucleic acids, in a patient and a control group preferably takes place under identical conditions, i.e. the levels of the polypeptides/proteins or nucleic acids in question are determined in samples derived from the patient and the control group under identical conditions, which are then further processed under identical conditions. Techniques for deriving and processing samples for determining levels of polypeptides, proteins and nucleic acids of interest are described herein and, particularly in the examples.

In a further aspect, the invention provides a ubiquitin fragment having a mass-to-charge ratio (m/z) of 6188 (ubiquitin m/z 6188) for use in a method for diagnosing a renal disease in a patient, wherein the method comprises determining the level of ubiquitin m/z 6188 in a sample of a patient, and wherein the substantial absence or reduced level of ubiquitin m/z 6188 compared to a control is indicative of the renal disease in said patient.

In yet a further aspect, the present invention provides ubiquitin m/z 6188 for use in a method for predicting the risk for a patient of developing a renal disease, wherein the method comprises determining the level of ubiquitin m/z 6188 in a sample derived from said patient, and wherein the substantial absence of ubiquitin m/z 6188 compared to a control is indicative of a risk for the patient of developing the renal disease.

In yet another aspect, the present invention provides ubiquitin ribosomal fusion protein UbA52 for use in a method for diagnosing a renal disease in a patient, wherein the method comprises determining the level of UbA52 in a sample of a patient, and wherein an elevated level of UbA52 compared to a control is indicative of the renal disease in said patient.

In yet another aspect, the present invention provides ubiquitin ribosomal fusion protein UbA52 for use in a method for predicting the risk for a patient of developing a renal disease, wherein the method comprises determining the level of ubiquitin ribosomal fusion protein UbA52 in a sample derived from said patient, and wherein an elevated level of UbA52 compared to a control is indicative of a risk for the patient of developing the renal disease.

In further preferred embodiments, the invention provides the use of ubiquitin m/z 6188 or UbA52 as defined above, wherein the methods for diagnosing a renal disease in a patient or the method for predicting the risk for a patient of developing a renal disease are as defined herein.

In another aspect, the present invention relates to a kit for diagnosing a renal disease in a patient or for predicting the risk of a patient for developing a renal disease, comprising (i) at least one antibody against at least one polypeptide of a group comprising ubiquitin m/z 6188, UbA52, and/or beta-2-microglobulin; (ii) at least one primer capable of specifically binding at least one nucleic acid of a group comprising a nucleic acid encoding ubiquitin m/z 6188, a nucleic acid encoding UbA52, and/or a nucleic acid encoding beta-2-microglobulin; or (iii) at least one peptide comprising at least one epitope of at least one polypeptide of a group comprising ubiquitin m/z 6188, UbA52, and/or beta-2-microglobulin.

In related embodiments, a kit of the present invention comprises (i) antibodies against at least two polypeptides of a group comprising ubiquitin m/z 6188, UbA52, and/or beta-2-microglobulin; (ii) at least two primers capable of specifically binding at least one nucleic acid of a group comprising a nucleic acid encoding ubiquitin m/z 6188, a nucleic acid encoding UbA52, and/or a nucleic acid encoding beta-2-microglobulin; or (iii) at least two peptides comprising at least one epitope of at least one polypeptide of a group comprising ubiquitin m/z 6188, UbA52, and/or beta-2-microglobulin.

In further related embodiments, a kit of the present invention comprises (i) antibodies against each of ubiquitin m/z 6188, UbA52, and beta-2-microglobulin; (ii) primers capable of specifically binding each of a nucleic acid encoding ubiquitin m/z 6188, a nucleic acid encoding UbA52, and/or a nucleic acid encoding beta-2-microglobulin; or (iii) peptides comprising at least one epitope of at least one polypeptide of each of ubiquitin m/z 6188, UbA52, and/or beta-2-microglobulin.

In a preferred embodiment, the kit of the invention is used in a method of diagnosing a renal disease in a patient or for predicting the risk of a patient for developing a renal disease. In further preferred embodiments, the kit of the invention is used in the methods as described herein.

In particular embodiments, the binding agent components of the kit, i.e, the antibodies, primers, or peptides, are immobilized on a solid support.

An "antibody" as used herein includes an antibody or antibody fragment such as a Fc fragment, an Fab fragment, or antigen-binding parts of an antibody. Suitable forms of antibodies and methods for producing various forms of antibodies are well known in the art, and include e.g. techniques such as immunizing a mammal with a polypeptide of the invention and isolating the resulting antibodies from the mammal, or techniques for producing monoclonal antibodies e.g. by the well-known hybridoma formation techniques. Antibodies can also be obtained by screening recombinant combinatorial immunglobulin libraries with polypeptides of the invention.

A "primer" as used herein refers to an oligonucleotide that is capable of specifically binding to a recognition site on a nucleic acid molecule, typically a DNA molecule. Typically, primers are between 10 and 150 nucleotides in length, and comprise a nucleic acid sequence that is complementary to a portion of the recognition site on the nucleic acid molecule of interest. The design and generation of suitable primers are well known in the art, and include the use of commercially available computer programs and techniques of DNA synthesis that are standard in the art. In the context of the present invention, a primer of the invention specifically binding to a recognition site on a nucleic acid molecule of the invention and is e.g. capable of serving as an initiator e.g. in a PCR reaction for elongation and/or amplification of the nucleic acid molecule of the invention.

A "peptide" as used herein in the context of a kit of the invention comprising at least one epitope of at least one polypeptide according to the invention, i.e. ubiquitin m/z 6188, UbA52, and/or beta-2-microglobulin. An epitope as used herein is also known as an antigenic determinant, and is the part or the features of a polypeptide of the invention that are recognized e.g. by antibodies. Preferably, the peptides of the invention are recognized, i.e. specifically bound, by antibodies that also recognize the polypeptides of the invention. Such antibodies may occur e.g. in body fluids of a patient such as blood plasma or serum. The size of an epitope and consequently a peptide of the invention can vary, and are typically between 10 and 100 amino acids. The location, sequence, and structure of epitopes can be mapped using various techniques known in the art, such as amino acid exchanges, protein microarrays, or ELISA techniques.

In a further aspect, the present invention relates to a method for determining the presence of a ubiquitin-degrading activity in a sample derived from a patient, comprising the steps of (i) obtaining a sample from said patient, (ii) adding exogenous ubiquitin to the sample under suitable conditions, (iii) determining the formation of a ubiquitin fragment having a mass-to-charge ratio (m/z) of 6188 (ubiquitin m/z 6188) in the sample, which formation is indicative of a ubiquitin-degradating activity in said sample.

A "ubiquitin-degrading activity" as used herein refers to an activity capable of converting the full-length form of ubiquitin, such as shown in SEQ ID NO:4, into a fragmented form ubiquitin m/z 6188, which preferably has SEQ ID NO:3. Preferably, this activity is monitored in a urine sample derived from a patient, and the activity is typically absent or substantially absent from the urine of patients suffering from diabetic nephropathy. It may be speculated that the ubiquitin-degrading activity is dependent on the activity of a protease, whose absence is specific for diabetic nephropathy.

The exogenous ubiquitin that is added to the sample is typically full-length human ubiquitin e.g. as shown in SEQ ID NO:4, and may be added in concentrations of between 0.1-10 pmol/µl. The determination of ubiquitin-degrading activity requires that the sample be kept under suitable conditions and further treated suitable, such as at a suitable temperature like room temperature, and a sufficient incubation time.

The invention also provides a kit for use in the method of determining the presence of a ubiquitin-degrading activity in a sample derived from a patient, comprising ubiquitin and means for determining the formation of ubiquitin m/z 6188. Such means may include an assay comprising antibodies suitable for recognizing non-fragmented ubiquitin and ubiquitin m/z 6188.

The following examples are meant to further illustrate, but not limit the invention. The examples comprise various technical features, and it will be appreciated that the invention relates to combinations of the technical features presented in this exemplifying section.

Materials and Methods

Study Population and Samples

Four patient groups were rigidly defined on the basis of the clinical course, microalbuminuria, and serum creatinine value. Table 1 gives an overview of the groups.

TABLE 1

Characteristics of patients whose urine was sampled for the study.

| | Diabetics with micro- or macroalbuminuria (N = 38) | Diabetics without micro- or macroalbuminuria (N = 45) | Patients with macro-albuminuria due to non-diabetic disease (N = 34) | Controls (N = 45) |
|---|---|---|---|---|
| Age (years) | 65 ± 11 | 60 ± 11 | 57 ± 20 | 40 ± 15 |
| Male/female | 25/13 | 28/17 | 20/14 | 26/19 |
| Albuminuria (mg/24 h) | 689.9 ± 341.2 | 6.5 ± 3.6 | 1320.9 ± 317.4 | <30 |

TABLE 1-continued

Characteristics of patients whose urine was sampled for the study.

| | Diabetics with micro- or macroalbuminuria (N = 38) | Diabetics without micro- or macroalbuminuria (N = 45) | Patients with macro-albuminuria due to non-diabetic disease (N = 34) | Controls (N = 45) |
|---|---|---|---|---|
| HbA1c | 9.4 ± 0.55 | 8.6 ± 0.37 | not tested | 4.9 |
| Retinopathy | 17 | 13 | 0 | 0 |
| Creatinine clearance (ml/min) | 117.3 ± 12.8 | 103.1 ± 16.8 | not tested | 112 |

Handling of Urine Samples for Proteomics Analysis

Clinical sample procurement and analysis as well as data management of this study were approved by the local Institutional Ethics Review Committee of the University Hospital of the Georg-August University, Goettingen, Germany.

For all our proteomics experiments, midstream urine was used due to the advantage of limiting protease activity. Urine collection was performed in 100 mL tubes supplied with protease inhibitors "Complete™ protease 1 tablet" from Roche (Roche, Indianapolis, USA). To decrease the protein degradation effect, 2 protease inhibitor tablets were dissolved in 1 mL 100 mM phosphate buffer and the dissolved protease cocktail was added to each 100 mL tube before collection of urine. After collection of urine, tubes were reversed immediately and gently to mix the protease inhibitors with the urine proteins. Subsequently, urine samples were centrifuged for 45 min by 3000×g and 4° C. After elimination of the precipitates, the supernatant was aliquoted in 10 mL portions and used immediately or stored at −80° C. until use.

Laboratory Methods 10 mL of each collected urine sample was used for the acquisition of the clinical chemical parameters including urine creatinine values, protein and albumin concentrations by using standard routine methods at the Institute of Clinical Chemistry or the laboratory of the Department of Nephrology & Rheumatology, Georg-August-University Goettingen, Germany.

Protein Profiling of Urine Samples Using Protein-Chip Arrays

For standardisation of urine sample handling, the clinical parameter microalbuminuria was used. All samples were adjusted to the same level of microalbuminuria (20 mg/L) before starting the profiling experiments. The samples were subsequently denatured for 15 min at 4° C. with 8 M urea in 40 mM Tris/HCl pH 7.2 supplemented with protease inhibitors. The protein profiling was performed as follows:

Strong anion-exchange (SAX2) protein arrays (Ciphergen Biosystems, Fremont, Calif., USA) were used for the analysis of differentially excreted proteins in urine from different patients by SELDI-TOF. 40 µL of the denatured urine samples were diluted in binding buffer (50 mM Tris-HCl, pH 8.5) in the manner 2 volume binding buffer/one volume sample. Prior to sample loading, the SAX2 arrays were equilibrated with 150 µL of binding buffer. 60 µL of the samples were applied to each spots in duplicates on the protein arrays by a 96-well bioprocessor (Ciphergen Biosystems). After 60 min incubation at room temperature on a platform shaker, the arrays were washed three times (5 min) in 150 µL of binding buffer before being quickly rinsed twice with 100 µL of distilled $H_2O$. The arrays were then removed from the bioprocessor system and air-dried. 1 µL of saturated sinapinic acid matrix prepared in 0.1% TFA with 50% acetonitrile was added twice to each spot. Proteins bound to the arrays were detected with a PBS II ProteinChip Reader (Ciphergen Biosystems) using an automated data collection protocol. Instrument settings were as follows: Laser intensity was set to 200 U, detector sensitivity to 8, focus mass to 15,000 Da. An average of 80 laser shots was collected per spot. Data were externally calibrated with a peptide mixture containing ACTH (18-39) ($[M+H]^+$2465.19), bovine insulin ($[M+H]^+$5733.5), bovine ubiquitin ($[M+H]^+$8564.8) bovine cytochrome C ($[M+H]^+$12230) for the lower molecular weight range and with myoglobin ($[M+H]^+$16951.5) horseradish peroxidase ($[M+H]^+$43240.0) and bovine albumin ($[M+H]^+$66433.0) for the high molecular weight range.

Reproducibility of the profiling data was guaranteed using the same instrument setting, batch of reagents, and Protein-Chip arrays and by analysing the urine samples within a short period of time. The samples were loaded in duplicate to monitor data reliability. All spectra were normalized according to their TIC (total ion count) and analysed using the ProteinChip Software version 3.0 (Ciphergen Biosystems).

Protein Precipitation and Estimation

Prior to the sample fractionation and enrichment of protein markers, total protein precipitation was performed. Five different urine aliquots per case were pooled together and 20 mL from the pooled urine were concentrated to 2 mL with an amicon column (Beverly, Mass., USA). Subsequently protein precipitation was carried out in 20% trichloroacetic acid in acetone. The protein concentrations were measured according to the Bradford method (Bradford M M. et al., 1976), using bovine serum albumin as standard.

Hydrophobic Fractionation

A 50 µL volume of RPC Poly-Bio beads (BioSepra) was equilibrated with 10% ACN/0.1% TFA. The sample fractions from the anion exchange fractionation containing the protein markers were adjusted to a final concentration of 10% ACN/0.5% TFA, and mixed with 50 µL of RPC beads for 30 min at room temperature. The tube was centrifuged for 1 min at 1000×g, and the supernatant was removed by aspiration. Bound proteins were eluted successively with 200 µL of 10%, 20%, 30%, 40%, and 50% ACN in 0.1% TFA. Proteins in the eluted fractions were detected by profiling 1 µL of each fraction on a NP20 ProteinChip Array.

For analytical investigations, sample fractions of interest were separated on SDS-PAGE prior to in gel digestion and mass spectrometry analysis. Gels were fixed and stained with a modified silver stain as previously described (Shevchenko A et al, 1996).

Anionic Exchange Fractionation

Prior to urine proteins fractionation 100 µL of Q HyperD® F resin (BioSepra) was added to a 1.0 mL column and equilibrated with 200 µL U1 buffer (1 M urea, 0.2% CHAPS, 50 mM Tris-HCl, pH 9). Each sample was prepared by dissolving the urine protein pellet in 150 µL of U2 buffer (9 M urea, 2% CHAPS, 50 mM Tris-HCl, pH 9). Each sample (150 µL total) was applied to an anion exchange column, and the column was gently mixed for 30 min. The flow-through fraction, containing unbound material, was eluted from the column by centrifugation at 1000×g for 1 min. Each column was washed with 200 µL of 50 mM Tris-HCl, pH 9, 0.1% Octylglucopyranosid (OGP) buffer regarded as pH 9 fraction (or fraction 1). The second wash step was carried out with 200 µL of 50 mM HEPES, pH 7, 0.1% OGP buffer to get the pH 7 fraction (or fraction 2). Subsequently the columns were washed with 200 µL of 100 mM NaAcetate, pH 5, 0.1% OGP buffer to obtain the pH 5 fraction (or fraction 3). The columns were then washed with 200 µL of 100 mM NaAcetate, pH 4, 0.1% OGP buffer resulting in the pH 4 fraction (or fraction 4). For gaining fraction 5 (pH 3), columns were washed with 200 µL of 50 mM NaCitrate, pH 3, 0.1% OGP buffer.

For analytical preparation, sample fractions of interest were separated on SDS-PAGE prior to in gel digestion and mass spectrometry analysis. Gels were fixed and stained with a modified silver stain as previously described (Shevchenko A, et al., 1996).

Passive Elution and Molecular Weight Control

To control the molecular weight of the identified proteins the gel bands with the proteins were cut and processed for passive elution as described previously (Dihazi H et al., 2007).

In-Gel Digestion and Peptide Sequence Analysis

In gel digestion and peptide extraction were carried out as described previously (Dihazi H et al., 2005b). Subsequently, the extracted peptides were subjected to peptide sequence analysis. The samples were dissolved in 0.1% formic acid and processed as described (Dihazi H et al., 2005). Processed data were searched against MSDB and Swissprot data bases through Mascot search engine using a peptide mass tolerance of 50 ppm (parts per million) and fragment tolerance of 100 mmu (millimass unit). Protein identifications with at least two peptides sequenced were considered significant.

SELDI-TOF MS Immuno-Capturing of Ubiquitin.

The SELDI immunoassay was performed according to Tolson et al. (2006) using urine from healthy donors, DM-NP and DM-WNP patients. Spectra were externally calibrated using bovine ubiquitin (m/z 8564.8) and bovine cytochrome C (m/z 12230.9).

Western Blot Analysis

The verification of the proteomic analysis data was performed by Western blot analysis. Mouse anti-ubiquitin monoclonal antibody (Sigma-Aldrich, Mo., USA) and horseradish peroxidase-linked sheep anti-mouse antibody (Amersham Biosciences, Freiburg, Germany) were used as primary and secondary antibodies, respectively.

Ubiquitin Degradation Assay

Urine samples were collected from healthy controls and from DM-NP patients with or without addition of protease inhibitors. 100 µl of each urine sample supplied with exogenous ubiquitin (1 pmol/µL) was incubated for different times at RT. Subsequently, the urine samples were prepared for the ProteinChip array as described above and the ubiquitin degradation in urine was monitored by sample profiling on SAX2 protein arrays.

Statistical Analysis

The protein profiles obtained from the different samples were normalized to the control group. The differences in the peak intensity for the various clusters were quantified using the nonparametric Mann-Whitney U-test implemented in the Biomarker Wizard software. The peak clusters differentially expressed between DM-NP and the other patients groups were used for classification analysis with Biomarker Patterns™ software (Ciphergen) as previously described (de Bont J M et al., 2006).

EXAMPLE 1

Reproducibility of the Protein-Pattern

The peak detection and data pre-processing of the proteins retained on the different protein arrays were carried out on a PBS-II mass reader. Acquisition of the highest mass was set to 150 kDa, with an optimization range from 5 to 20 kDa. A mass accuracy of 0.1% was achieved by external calibration. Since reproducibility of the protein pattern depends on the sample collection procedures, we optimized a urine handling protocol which allows fast collection and processing of urine leading to almost total inhibition of protein degradation and good reproducibility of the data. The mass spectra of the sample from the same urine were identical in their quality and quantity of protein/peptide peaks. 52 peak clusters or common peaks (signal-to-noise ratio>5) were generated from the identified peaks using the Biomarker Wizard Software (Ciphergen). It was found that most of the peaks were detected between m/z 2000-20000 and they were considered the most useful for protein profiling. The average coefficient of variances (CVs) of reliable peaks in the urine control obtained from different samples and laser power settings were determined on 8 protein peak clusters present in all different urine samples, measured in 8 independent experiments. The CVs of the peak intensities for the 8 peak clusters ranged from 12% to 32% and did not differ statistically between the different sample and laser settings.

EXAMPLE 2

Protein Expression Patterns in Normal and Pathological Urines

A total of 45 type 2 DM without diabetic nephropathy and without proteinuria, 38 DM-NP, 34 patient with proteinuria and without nephropathy, and 45 healthy controls were analysed on SAX2 ProteinChip arrays. From all protein peaks detected 15 had low p-values in different statistical tests ($p<0.001$ in Student's t-test) (see Table 2) indicating strong statistical significance of differential protein release in urine.

TABLE 2

Fifteen statistically significant mass peaks differentially excreted in the urine of DM NP and the three other groups of patients

| m/z | p-value |
| --- | --- |
| 6188 | 0.0000004470 |
| 4135 | 0.0000041068 |
| 11774 | 0.0000041556 |
| 5380 | 0.0000247278 |
| 2761 | 0.0000290346 |
| 5429 | 0.0000490876 |
| 4533 | 0.0000666605 |
| 67826 | 0.0000794876 |
| 14766 | 0.0000811556 |
| 8605 | 0.0001042392 |
| 5794 | 0.0001584215 |
| 3495 | 0.0002321087 |
| 5027 | 0.0004465295 |
| 3986 | 0.0007065911 |
| 10869 | 0.0009570105 |

Special focus was on proteins differentiating the DM-NP patients from the rest of the sample groups. The analysis revealed striking expression patterns in a subset of DM-NP urine samples as exemplified as spectral views in FIG. 1 for a set of prominent peaks with the m/z 6188 (FIG. 1A), 11774, and 14766 (FIG. 1B).

Figure 2:
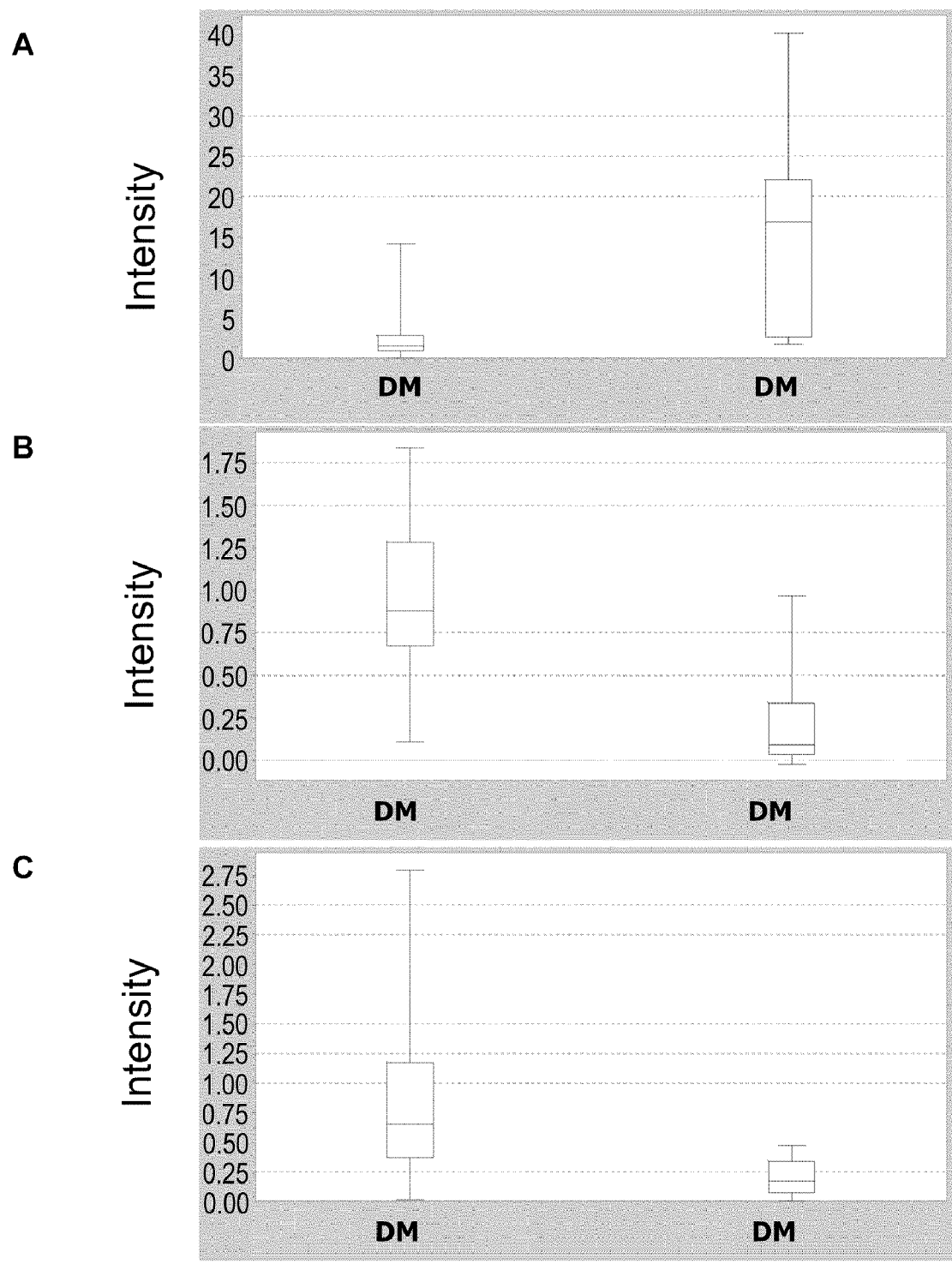
FIG. 2. Differential expression of the three mass peaks (m/z 6188, 11774, and 14766) in urine from DM-NP and DM-WNP patients. Box plots of relative intensities of (A), m/z 6188 (B), m/z 11774 and (C), m/z 14766 as detected by SELDI-TOF analysis of 38 DM-NP and 45 DM-WNP urine samples. The lines represent the median value within each group.
Figure 6:
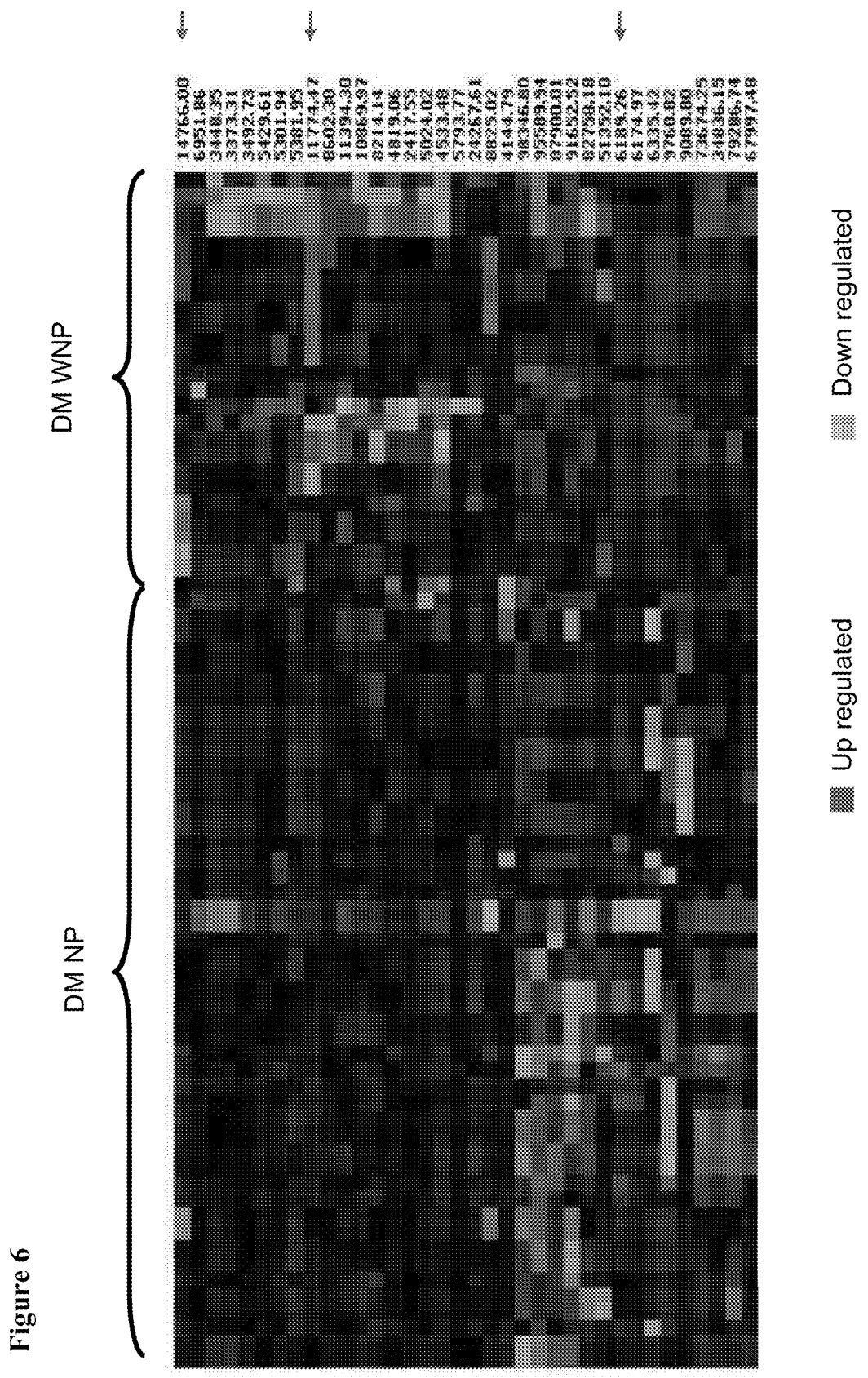
Figure 7:
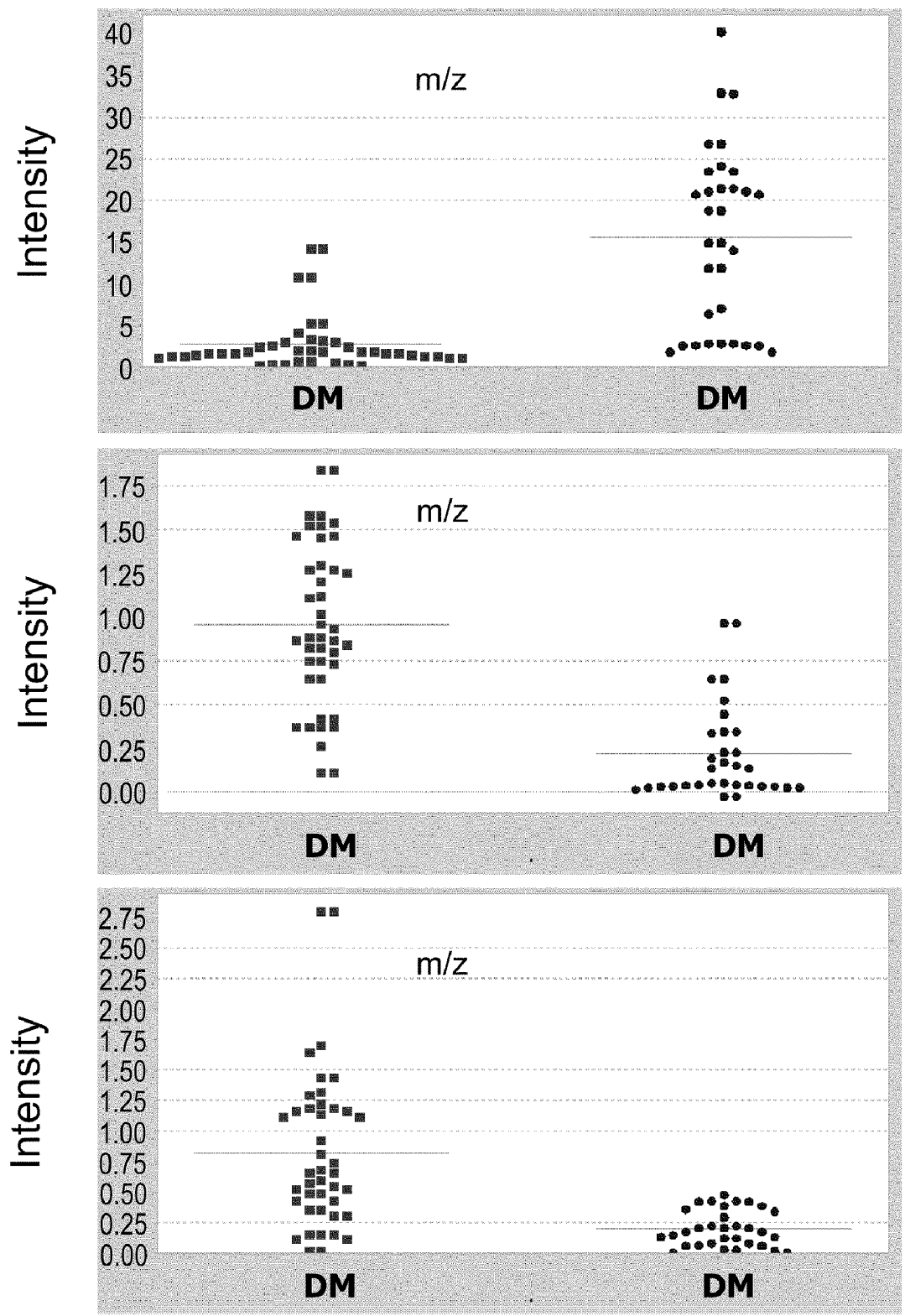
FIG. 7. Differential expression of the three mass peaks (m/z 6188, 11774, and 14766) in urine from DM-NP and DM-WNP patients.
Figure 8:
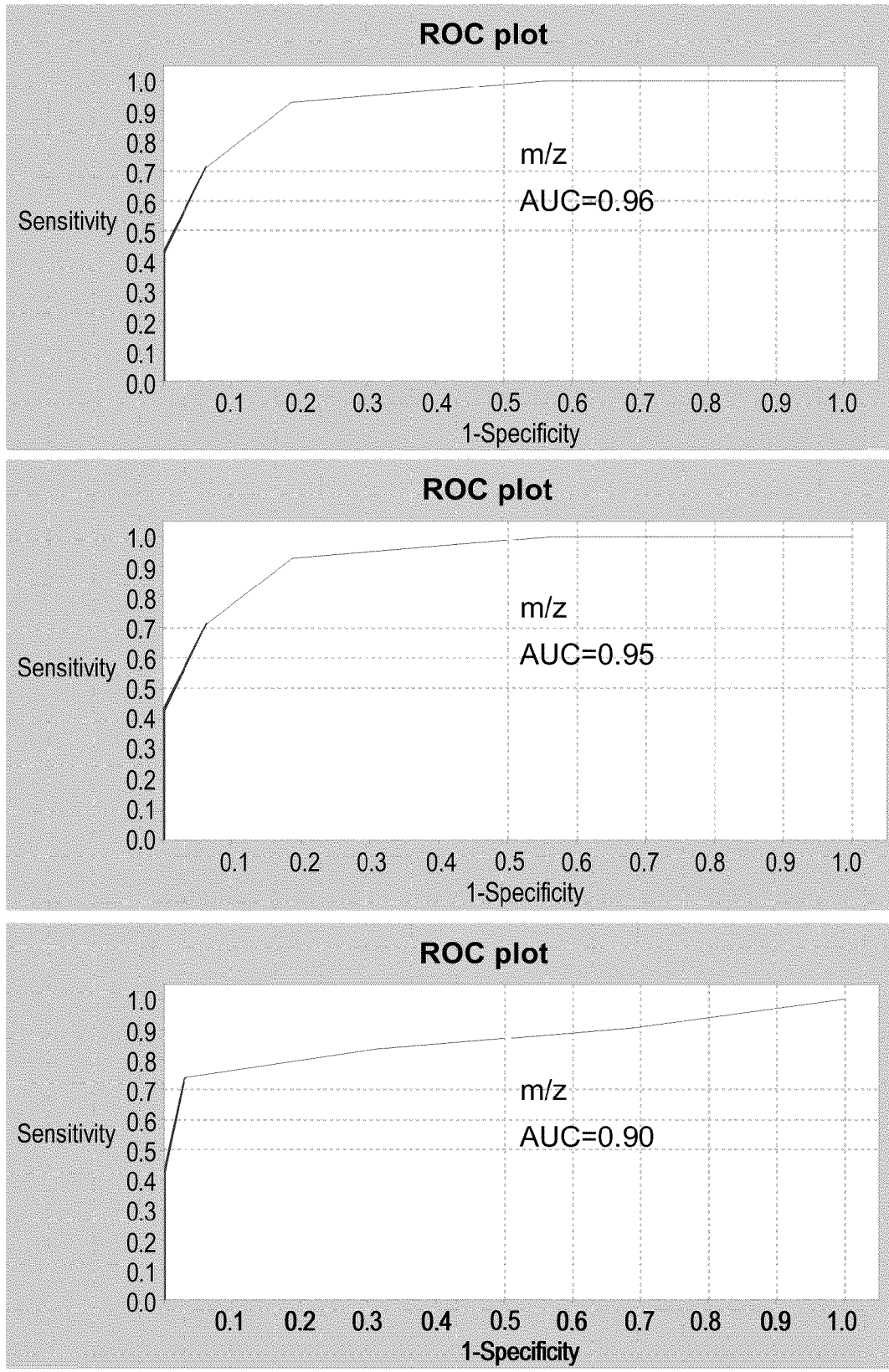
FIG. 8. The diagnostic value for all these three peaks was demonstrated in highly significant receiver operated characteristic (ROC) plots showing areas under the curves (AUC) well above 0.9.

A heat map from DM-NP and DM-WNP was generated (See FIG. 6). The three mentioned peaks are indicated on the map. These could clearly discriminate the two sample groups. The m/z 6188 is down-regulated in DM-NP samples compared to DM-WNP, whereas the proteins with m/z 11774 and 14766 showed a strong negative correlation to the smaller protein with m/z 6188. Quantitatively, the average normalized intensities of the peak with m/z 6188 were several folds lower in DM-NP compared with other groups (FIG. 2A). Conversely, the m/z 14766 intensities were higher in DM-NP patients and lower in all other groups (FIG. 2C). The peak m/z 11774 was clearly higher in DM-NP and non-diabetic proteinuria patients than the other groups (FIG. 2B). With few exceptions (6 samples), none of the DM-NP samples showed significant excretion of the protein with m/z 6188 in urine. The diagnostic value for all these three peaks was demonstrated in highly significant receiver operated characteristic (ROC) plots showing areas under the curves (AUC) well above 0.9 (see FIGS. 7 and 8).

Figure 9:
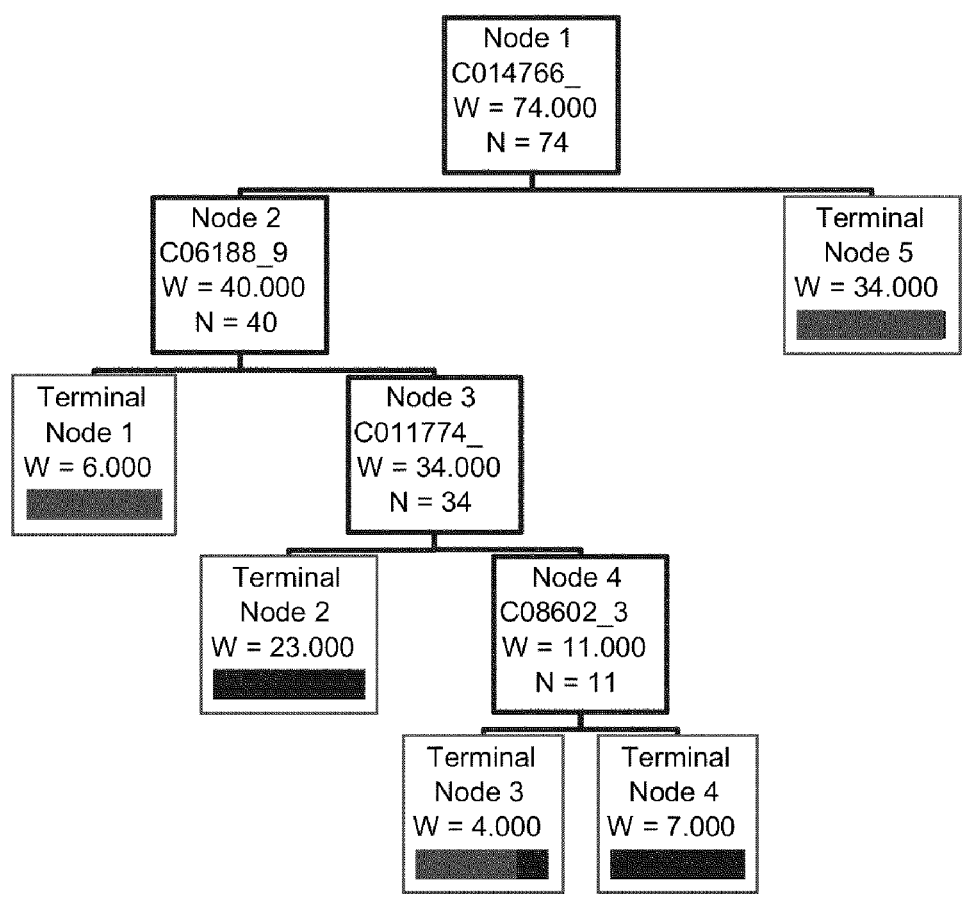
FIG. 9. Diagram of a decision tree for the classification of the DM NP and DM WNP. In bold outline the primary nodes and in thin outline the terminal nodes. It was noted that the protein found to be differentially excreted in urine of this two groups were included as primary splitters in all classification trees generated during the analysis and they almost separated the majority of the samples into 2 groups. The tree represent the most optimal classification using peaks with best p-values (m/z 6188, 8602, 11774, and 14766). The selected classification used 4 splitters with distinct masses of m/z 14766, 6188, 11774, and 8602 respectively, and classified the cases into 5 terminal nodes. The error rate of the generated classification tree was estimated through a process of cross-validation.

A classification tree was created from the training set to discriminate DM-NP and DM-WNP groups. The selected classification tree used 4 splitters with distinct masses of m/z 14766, 6188, 11774, and 8602 respectively, and classified the cases into 5 terminal nodes (see FIG. 9). The error rate of the generated classification tree was estimated through a process of cross-validation.

EXAMPLE 3

Purification and Identification of Differentially Expressed Proteins

Figure 3:
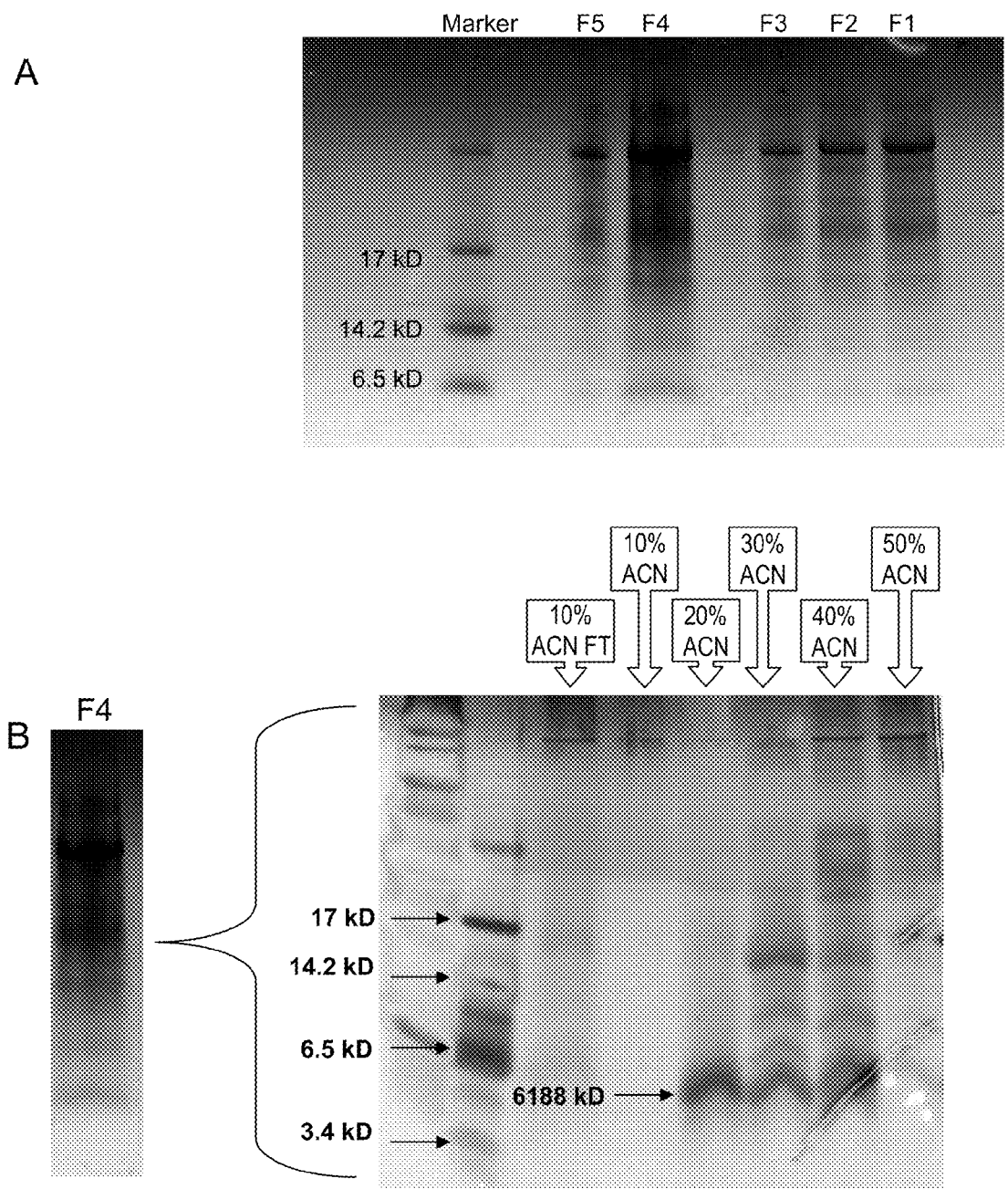
Figure 4:
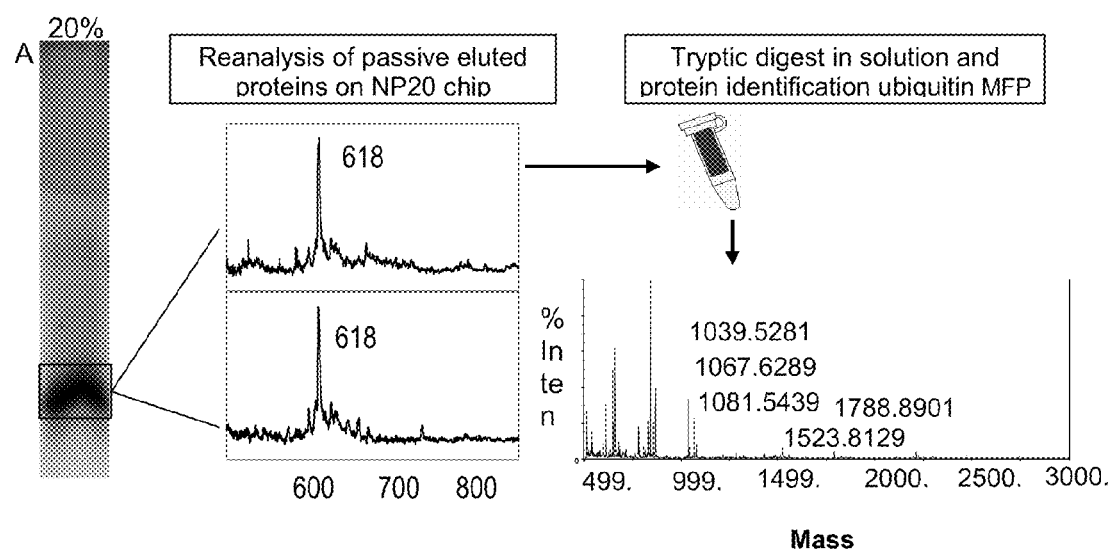
FIG. 4. Identification of proteins by MS. (A), the protein band in arrow was excised from the gel and submitted to passive elution before tryptic digest and protein identification. The proteins were analysed on normal phase (NP20) array by SELDI-TOF MS. The peaks showing masses of m/z 6188 were identical to the protein peaks of interest in SELDI-TOF MS. The tryptic digest from peak m/z 6188 generated the mass fingerprint (MFP) identifying the protein as ubiquitin. The peptide mass sequencing confirms the MFP results. (B), representative product ion mass spectrum from the doubly charged tryptic precursor peaks of m/z 534.35, m/z 894.49 and m/z 541.32 from the 6188 Da ubiquitin showed a complete y- and b-ion series corresponding to the sequences ESTLHLVLR, TITLEVEPSDTIENVK and TLSDYNIQK respectively.
Figure 11:
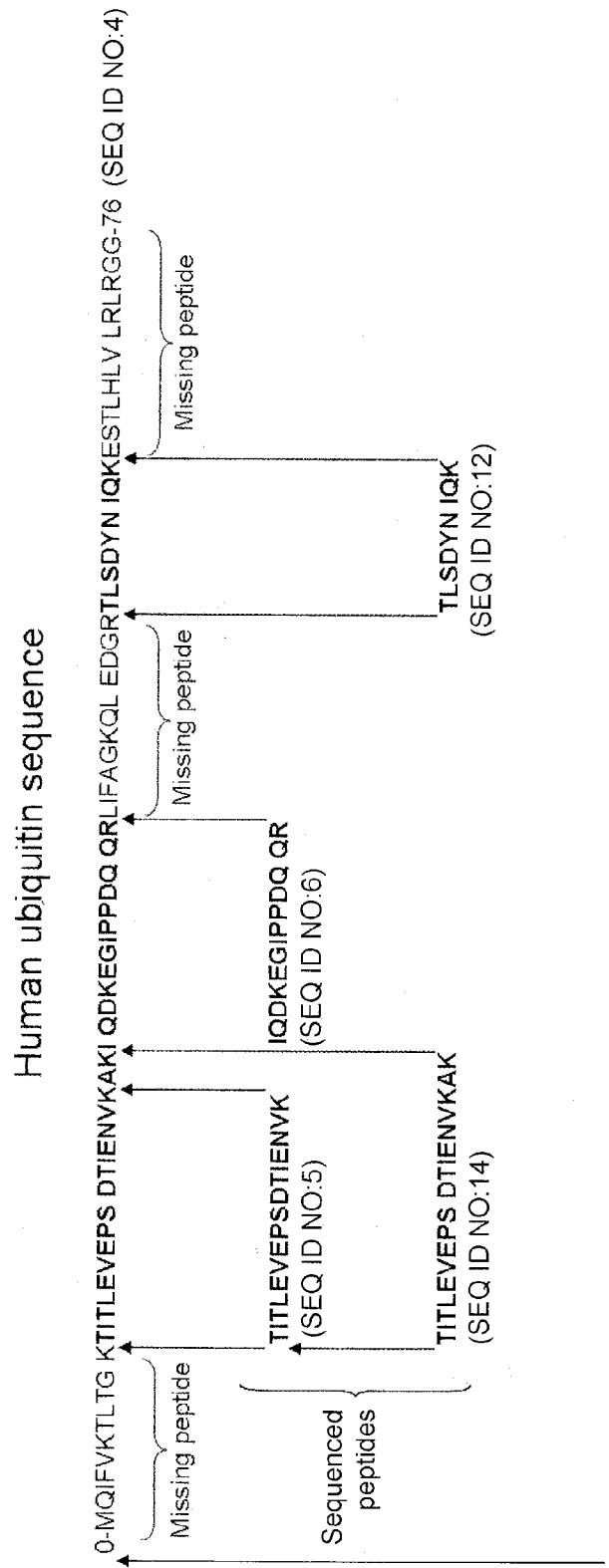
FIG. 11. Identified peptides and sequence coverage of ubiquitin. The ubiquitin is a 76 amino acid large protein. The peptide fragment sequencing allowed the confirmation of the middle part of the protein. The N- and C-terminal parts could not be detected. The sequenced peptides are indicated in bold.

To purify and identify differentially excreted proteins from pathological and healthy urine, samples were selected in which the protein peaks of interest were present in high abundance. These samples were fractionated by anion exchange and reverse phase chromatography as described in the "Materials and Methods" section. After the anion exchange fractionation, the fraction containing large amounts of the protein of interest e.g. F4 for m/z 6188 (FIG. 3A) was used for the second fractionation. The reverse phase elutes showed high amounts of the protein m/z 6188 in the fraction with 20% ACN in elution buffer (FIG. 3B). This fraction was used for passive elution from the gel and molecular weight control of the protein. Subsequently the rest of the eluate served for in gel digestion and mass spectrometry analysis to identify the protein (FIG. 4). Both MALDI-TOF MS and ESI-MS/MS analysis allowed the identification of the m/z 6188 as ubiquitin, m/z 11774 as β-2-microglobulin (β-2M) and m/z 14766 as ubiquitin and ribosomal protein L40. The MALDI-TOF MS derived peptide fingerprint for ubiquitin (m/z 6188) is shown in FIG. 4. The ubiquitin has a theoretical molecular weight of 8565 Da, the ubiquitin identified in urine has a mass of 6188 Da. The identification of the ubiquitin was based on MS/MS sequencing of selected tryptic peptides, 3 peptides/protein could be sequenced. The fragmentation of the doubly charged tryptic peaks of m/z 534.35, m/z 894.49 and m/z 541.32 from the 6188 Da ubiquitin showed a complete y- and b-ion series corresponding to the sequences ESTLHLVLR, TITLEVEPSDTIENVK and TLSDYNIQK respectively (FIG. 11). In addition, the high Mascot score (up to 91) and extensive sequence coverage (up to 53%) demonstrate a high level of confidence in the protein identification. The summary of the MS/MS sequencing analysis of all three proteins is given (see Table 3).

TABLE 3

Summary of the identification of the proteins with high discrimination power. Protein name, accession number, amino acid composition of the sequenced peptides, identification score, calculated and observed mass of the peptides are given.

| Protein | Swiss-Prot entry | Score | Sequenced peptides | Calc mass (kDa) | Observed mass (kDa) |
|---------|------------------|-------|--------------------|-----------------|---------------------|
| Ubiquitin | P62988 | 91 | TITLEVEPSDTIENVK | 1786.92 | 1786.79 |
|  |  |  | IQDKEGIPPDQQR | 1522.77 | 1522.64 |
|  |  |  | EGIPPDQQR | 1038.50 | 1038.43 |
| Beta-2-microglobulin | P61769 | 182 | IEKVEHSDLSFSK | 1517.77 | 1517.70 |
|  |  |  | VEHSDLSFSK | 1147.55 | 1147.43 |
|  |  |  | DWSFYLLYYTEFTPTEK | 2202.01 | 2201.98 |
|  |  |  | VNHVTLSQPK | 1121.61 | 1121.60 |
| UbA52 ubiquitin and ribosomal fusion protein | P62988 | 121 | TITLEVEPSDTIENVK | 1786.92 | 1786.97 |
|  |  |  | IQDKEGIPPDQQR | 1522.77 | 1522.87 |
|  |  |  | EGIPPDQQR | 1038.50 | 1038.58 |
|  |  |  | TLSDYNIQK | 1080.54 | 1080.62 |
|  |  |  | ESTLHLVLR | 1066.61 | 1066.68 |

Our data support the hypothesis that the increased expression of UbA52 in tubular cells of DM-NP patients combined with acute tubular injury and cell apoptosis results in alteration of UbA52 level in urine of diabetic nephropathy patients. Further, our results confirm the alteration of β2-M level in urine of patients with DM-NP and in patients with proteinuria due to non-diabetic renal disease. In addition to UbA52, another ubiquitin form was found to be released in lower amount in urine of DM-NP compared to the three other groups. The ubiquitin 6188 Da is smaller than the known ubiquitin 8565 Da. We hypothesize that the progressive disappearance of ubiquitin with m/z 6188 from urine correlates with the progressive appearance of UbA52 in urine and the progression of diabetic nephropathy. Furthermore, these data support the presence of a protease in control urine which is responsible for the ubiquitin degradation; this protease is missing or is present in low amount in DM-NP urine. Because of the degradation of short-lived and abnormal proteins, ubiquitination and ubiquitin-proteasome pathway control many processes including proteolysis and intracellular trafficking. Ubiquitin specific proteases are likely to be central in the regulation of all processes in which ubiquitin is involved. The protease responsible for the degradation of ubiquitin to ubiquitin 6188 Da is still not known and the role of the short form of ubiquitin in the protein degradation system remains a matter of further investigations.

EXAMPLE 4

Figure 10:
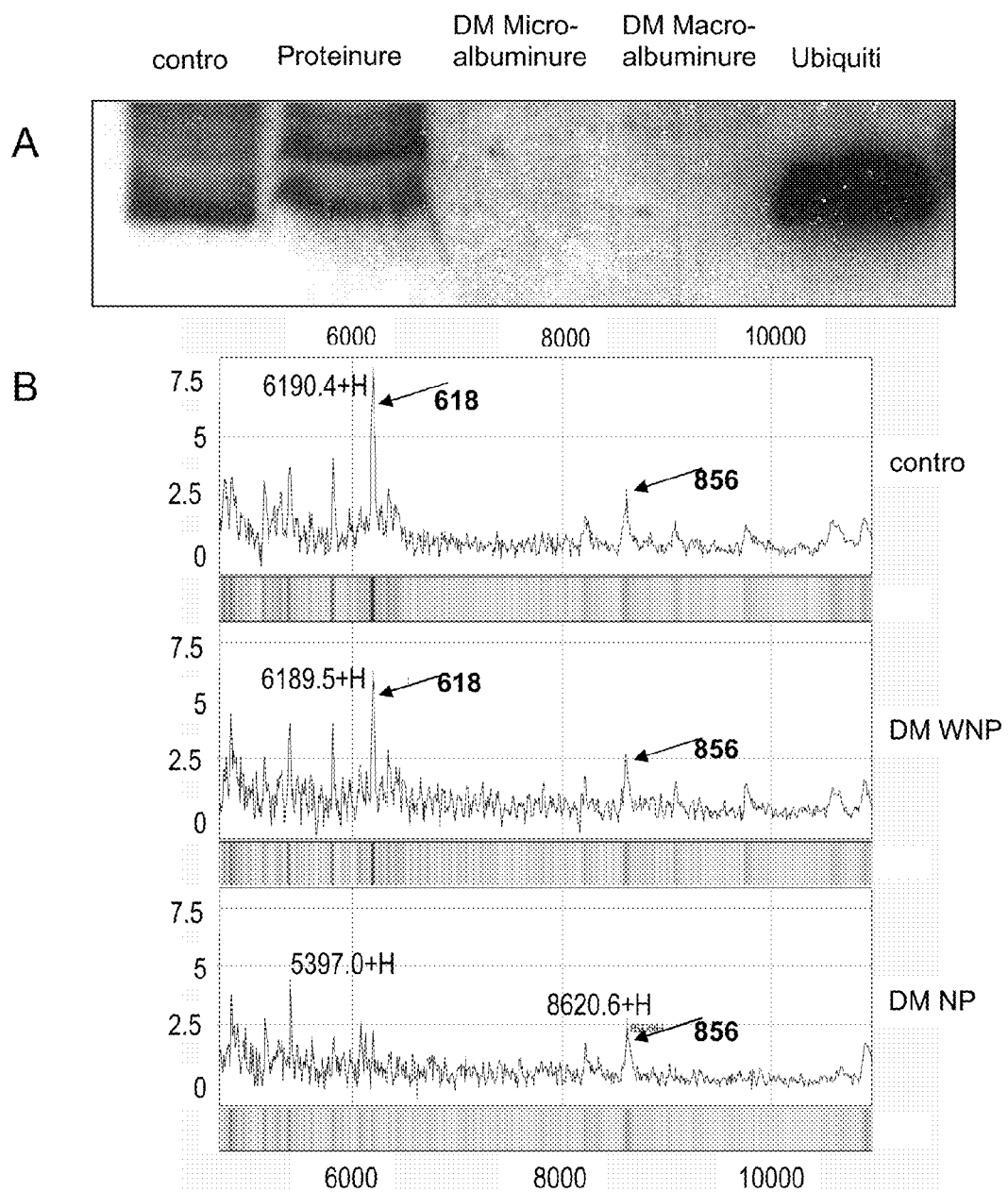
FIG. 10. Validation of the protein discriminating the DM NP patients from the other groups. (A), Western blot analysis of the urine samples from different groups with the anti-ubiquitin antibody. (B), On-chip immunoassay with the ubiquitin antibody: After binding the protein A and anti-ubiquitin antibody to the PS10 Chip urine samples from DM NP, DM WNP and healthy controls were loaded onto the chip and incubated for 1 h under shaking. The matrix was added after washing. The binding of ubiquitin was then controlled with the ProteinChip Biology System Reader.

Validation of the Differential Ubiquitin Excretion by Western Blot and SELDI-TOF MS Immuno-Capturing In order to validate the differential excretion of m/z 6188 ubiquitin in DM-NP urine compared to the other groups, Western blotting was performed on pooled samples from each group. In the case of DM-NP, patients with almost no m/z 6188 peak were chosen for the analysis. Ubiquitin was highly excreted in the urine of the DM-WNP, in healthy controls and proteinuria patients (See FIG. 10A). DM-NP patients release non detectable amounts of m/z 6188 ubiquitin (See FIG. 10A). Similar results were found when using SELDI-TOF MS immuno-capturing of ubiquitin. In this case a very low amount of m/z 8565 ubiquitin could be detected in the urine of DM-NP patients but almost no m/z 6188 ubiqutin (See FIG. 10B).

EXAMPLE 5

Ubiquitin Degradation Assay

Figure 5:
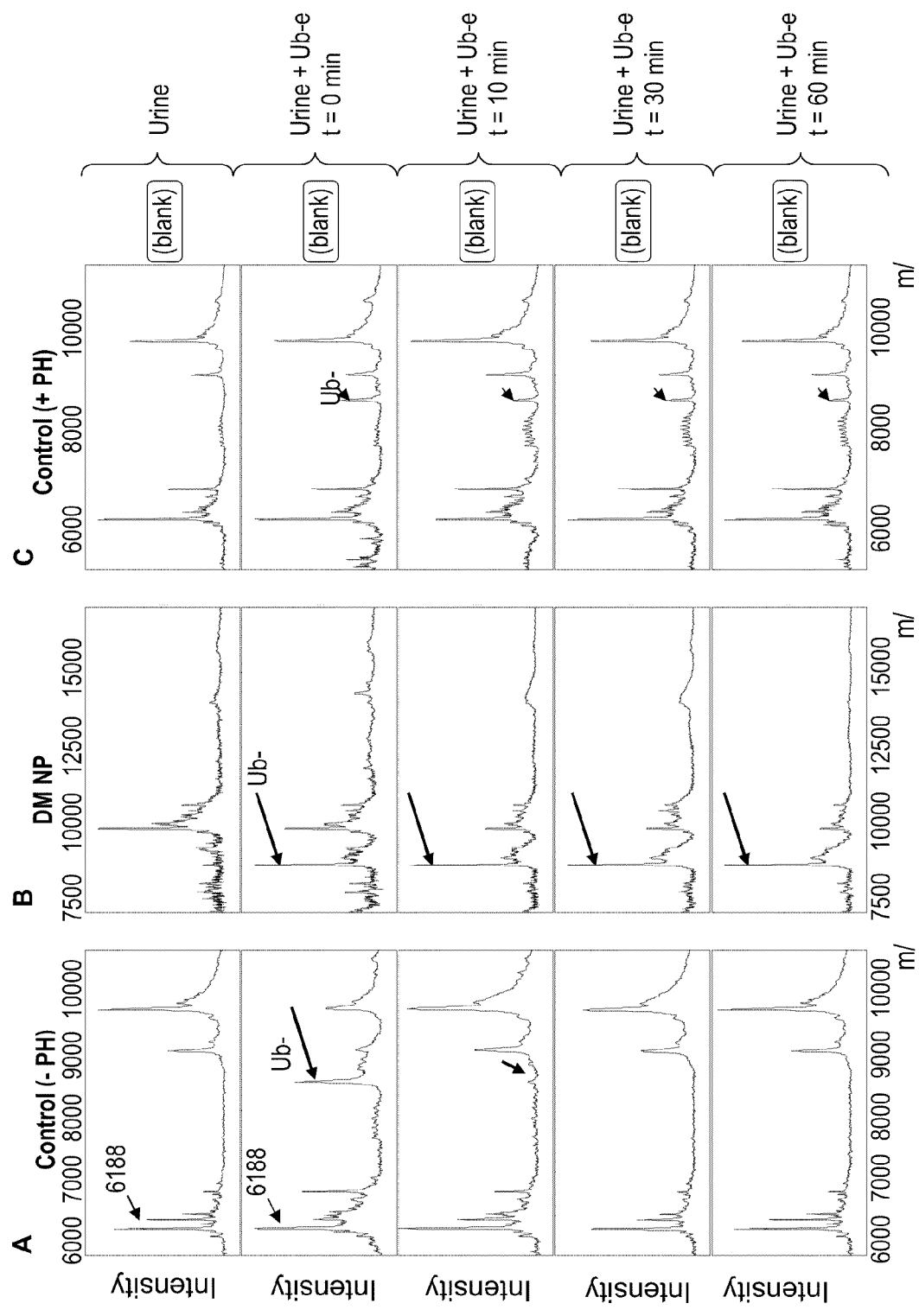
FIG. 5. Ubiquitin degradation assay. Urine samples from healthy controls and DM-NP patients were collected with and without protease inhibitors. Subsequently the samples were supplied with exogenous ubiquitin and incubated for different time periods at RT. (A), control urine without protease inhibitors. Exogenous ubiquitin shows strong degradation within the first 10 min. (B), the DM-NP urine spectra show almost no degradation of exogenous ubiquitin even after 1 hour incubation. (C), protease inhibitors impede exogenous ubiquitin degradation in control urine. Ub-e: exogenous Ubiquitin FIG. 6. Hierarchical clustering of SELDI-TOF MS protein expression data from DM NP and DM WNP. Intensities of the peaks were median centre. Average dot product and average linkage were used for clustering. Red to green represents log peak intensity from −1 to 1. Number labels on the right are m/z of the significant peaks. The Clustering algorithm groups the urine samples in two main clusters. Cluster 1 containing the main group of DM NP patients and only two DM WNP patients. Cluster 2 shows DM WNP only. The mass peaks indicated on the figure with the arrows and identified in FIG. 1 as potential markers are clearly differentially expressed in the two groups.

To investigate whether the 6188 Da ubiquitin is a degradation product or a splice form of the normal ubiquitin, we performed an ubiquitin degradation assay as described in "Materials and Methods". In control urine without protease inhibitors the ubiquitin was degraded within 10 min and the peak with m/z 6188 increased in intensity (FIG. 5A). Conversely, urine spectra from DM-NP patients showed almost no degradation of ubiquitin even after one hour incubation at RT (FIG. 5B). Addition of protease inhibitors blocks the ubiquitin degradation in control urine (FIG. 5C).

List of References

The references listed below are hereby incorporated by reference in their entireties.

1. Mykkanen L, Haffner S M, Kuusisto J, Pyorala K, Laakso M. Microalbuminuria precedes the development of NIDDM. Diabetes 1994; 43:552-7.
2. Thongboonkerd V, Barati M T, McLeish K R, Pierce W M, Epstein P N, Klein J B. Proteomics and diabetic nephropathy. Contrib Nephrol 2004; 141:142-54.
3. Thongboonkerd V, Malasit P. Renal and urinary proteomics: current applications and challenges. Proteomics 2005; 5:1033-42. Dihazi H. Clinical proteomics: an insight into the urinary proteome. Interview with Dr. Hassan Dihazi. Expert Rev Proteomics 2006; 3:481-2.
4. Susztak K, Bottinger E P. Diabetic nephropathy: a frontier for personalized medicine. J Am Soc Nephrol 2006; 17:361-7.
5. Hong C Y, Hughes K, Chia K S, Ng V, Ling S L. Urinary alpha1-microglobulin as a marker of nephropathy in type 2 diabetic Asian subjects in Singapore. Diabetes Care 2003; 26:338-42.
6. Rossing K, Mischak H, Parving H H, Christensen P K, Walden M, Hillmann M, Kaiser T. Impact of diabetic nephropathy and angiotensin II receptor blockade on urinary polypeptide patterns. Kidney Int 2005; 68:193-205.
7. Dihazi H, Sandra Lindner, Markus Meyer, Asif Abdul Rahman, Gerhard Anton Mueller and Frank Strutz. Characterization of diabetic nephropathy by urinary proteomic analysis: identification of Biomarkers. 3rd World Congress of Nephrology, 2005. (Dihazi 2005a)
8. Sun L, Pan X, Wada J, Haas C S, Wuthrich R P, Danesh F R, et al. Isolation and functional analysis of mouse UbA52 gene and its relevance to diabetic nephropathy. J Biol Chem 2002; 277:29953-62.
9. Schardijn G, Statius van Eps L W, Swaak A J, Kager J C, Persijn J P. Urinary beta 2 microglobulin in upper and lower urinary-tract infections. Lancet 1979; 1:805-7.
10. Schardijn G H, Statius van Eps L W. Beta 2-microglobulin: its significance in the evaluation of renal function. Kidney Int 1987; 32:635-41.
11. Schaub S, Rush D, Wilkins J, Gibson I W, Weiler T, Sangster K, et al. Proteomic-based detection of urine proteins associated with acute renal allograft rejection. J Am Soc Nephrol 2004; 15:219-27.
12. Hong C Y, Chia K S. Markers of diabetic nephropathy. J Diabetes Complications 1998; 12:43-60.
13. Bradford M M. A rapid and sensitive method for the quantitation of microgram quantities of protein utilizing the principle of protein-dye binding. Anal Biochem 1976; 72:248-54.
14. Shevchenko A, Wilm M, Vorm O, Mann M. Mass spectrometric sequencing of proteins silver-stained polyacrylamide gels. Anal Chem 1996; 68:850-8.
15. Dihazi H, Muller G A. Urinary proteomics: a tool to discover biomarkers of kidney diseases. Expert Rev Proteomics 2007; 4:39-50.
16. Dihazi H, Asif A R, Agarwal N K, Doncheva Y, Muller G A. Proteomic analysis of cellular response to osmotic stress in thick ascending limb of Henle's loop (TALH) cells. Mol Cell Proteomics 2005; 4:1445-58. (Dihazi 2005b)
17. Tolson J P, Flad T, Gnau V, Dihazi H, Hennenlotter J, Beck A, et al. Differential detection of S100A8 in transitional cell carcinoma of the bladder by pair wise tissue proteomic and immunohistochemical analysis. Proteomics 2006; 6:697-708.
18. de Bont J M, den Boer M L, Reddingius R E, Jansen J, Passier M, van Schaik R H, et al. Identification of apolipoprotein A-II in cerebrospinal fluid of pediatric brain tumor patients by protein expression profiling. Clin Chem 2006; 52:1501-9.
19. Muller G A, Muller C A, Dihazi H. Clinical proteomics—on the long way from bench to bedside? Nephrol Dial Transplant 2007.
20. U.S. Pat. No. 5,359,681
21. Pierce Immunotechnology Catalog and Handbook, 1991, at A12-A13
22. Sackett et al., *Clinical Epidemiology: A Basic Science for Clinical Medicine*, Little Brown and Co., 1985, p. 106-7.

What is claimed is:

1. A method for diagnosing diabetic nephropathy in a patient or for predicting the risk of a patient for developing diabetic nephropathy, comprising determining the level of a ubiquitin fragment having a mass-to-charge ratio (m/z) of 6188 (ubiquitin m/z 6188) in a sample derived from said patient,
   wherein the sample is a urine sample, a kidney tissue sample or a kidney tissue biopsy,
   wherein the substantial absence or a reduced level of less than 25% of ubiquitin m/z 6188 compared to a control is indicative of diabetic nephropathy in said patient or is indicative of a risk for the patient of developing diabetic nephropathy.

2. The method of claim 1, further comprising
   (i) determining the level of beta-2-microglobulin (SEQ ID NO: 2), or the level of a nucleic acid encoding beta-2-microglobulin, compared to a control: or
   (ii) determining the level of ubiquitin ribosomal fusion protein UbA52(SEQ ID NO: 1), or the level of a nucleic acid encoding UbA52, compared to a control; or
   (iii) determining the level of both beta-2-microglobulin and UbA52, or the level of both a nucleic acid encoding beta-2-microglobulin and a nucleic acid encoding UbA52, compared to a control:
   wherein an elevated level of beta-2-microglobulin and/or UbA52, or an elevated level of a nucleic acid encoding beta-2-microglobulin and/or a nucleic acid encoding UbA52, is indicative of diabetic nephropathy in said patient or is indicative of a risk for the patient of developing diabetic nephropathy.

3. The method of claim 1, further comprising
   (i) determining the level of beta-2-microglobulin (SEQ ID NO: 2) compared to a control; or
   (ii) determining the level of ubiquitin ribosomal fusion protein UbA52(SEQ ID NO: 1) compared to a control; or
   (iii) determining the level of both beta-2-microglobulin and UbA52 compared to a control;
   wherein an elevated level of beta-2-microglobulin and/or UbA52 is indicative of diabetic nephropathy in said patient or is indicative of a risk for the patient of developing diabetic nephropathy;
   the method further comprising
   (a) in (ii) or (iii) determining the ratio of the level of ubiquitin m/z 6188 to the level of UbA52, wherein a ratio of less than 5 is indicative of diabetic nephropathy in said patient;
   (b) in (ii) or (iii) determining the ratio of the level of ubiquitin m/z 6188 to the level of UbA52, wherein a ratio of less than 85 is indicative of a risk for the patient of developing diabetic nephropathy;
   (c) in (i) or (iii) determining the ratio of the level of ubiquitin m/z 6188 to the level of beta-2-microglobulin, wherein a ratio of less than 5 is indicative of diabetic nephropathy in said patient; or
   (d) in (i) or (iii) determining the ratio of the level of ubiquitin m/z 6188 to the level of beta-2-microglobulin, wherein a ratio of less than 70 is indicative of a risk for the patient of developing diabetic nephropathy.

4. The method of claim 1, further comprising determining the ratio of the level of ubiquitin m/z 6188 to the level of UbA52, in a patient and a control group under identical conditions, wherein a ratio of less than 85 in the patient and a ratio of at least 85 in the control group is indicative of diabetic nephropathy in said patient or is indicative of a risk for the patient of developing diabetic nephropathy.

5. The method of claim 1, further comprising determining the ratio of the level of ubiquitin m/z 6188 to the level of beta-2-microglobulin in a patient and a control group under identical conditions, wherein a ratio of less than 70 in the patient and a ratio of at least 70 in the control group is indicative of diabetic nephropathy in said patient or is indicative of a risk for the patient of developing diabetic nephropathy.

6. The method of claim 1, wherein diabetic nephropathy is a combination of diabetic nephropathy and tubular nephropathy.

7. The method of claim 1, wherein the patient is a diabetic patient, a diabetic patient showing symptoms of nephropathy, a diabetic patient without symptoms of nephropathy and/or microalbuminuria, a patient showing proteinuria due to non-diabetic disease, or a patient showing no symptoms of diabetes or renal disease.

8. A method for diagnosing diabetic nephropathy in a patient or for predicting the risk of a patient for developing diabetic nephropathy, comprising determining the level of ubiquitin ribosomal fusion protein UbA52(SEQ ID NO: 1), or the level of a nucleic acid encoding UbA52, in a sample derived from said patient,
   wherein the sample is a urine sample, a kidney tissue sample or a kidney tissue biopsy,
   wherein an elevated level of UbA52 or the nucleic acid encoding UbA52 compared to a control is indicative of diabetic nephropathy in said patient or is indicative of a risk for the patient of developing diabetic nephropathy,
   further comprising
   (i) determining the level of ubiquitin m/z 6188 compared to a control; or
   (ii) determining the level of beta-2-microglobulin (SEQ ID NO: 2) compared to a control; or
   (iii) determining the level of both ubiquitin m/z 6188 and beta-2-microglobulin compared to a control;
   the method further comprising
   (a) in (i) or (iii) determining the ratio of the level of ubiquitin m/z 6188 to the level of UbA52, wherein a ratio of less than 5 is indicative of diabetic nephropathy in said patient;
   (b) in (i) or (iii) determining the ratio of the level of ubiquitin m/z 6188 to the level of UbA52, wherein a ratio of less than 85 is indicative of a risk for the patient of developing diabetic nephropathy;
   (c) in (iii) determining the ratio of the level of ubiquitin m/z 6188 to the level of beta-2-microglobulin, wherein a ratio of less than 5 is indicative of diabetic nephropathy in said patient; or
   (d) in (iii) determining the ratio of the level of ubiquitin m/z 6188 to the level of beta-2-microglobulin, wherein a ratio of less than 70 is indicative of a risk for the patient of developing diabetic nephropathy.

9. The method of claim 8, further comprising determining the level of a nucleic acid encoding beta-2-microglobulin, compared to a control;
   wherein an elevated level a nucleic acid encoding beta-2-microglobulin is indicative of diabetic nephropathy in said patient or is indicative of a risk for the patient of developing diabetic nephropathy.

10. The method of claim 8, wherein diabetic nephropathy is a combination of diabetic nephropathy and tubular nephropathy.

11. The method of claim 8, wherein the patient is a diabetic patient, a diabetic patient showing symptoms of nephropathy, a diabetic patient without symptoms of nephropathy and/or microalbuminuria, a patient showing proteinuria due to non-diabetic disease, or a patient showing no symptoms of diabetes or renal disease.

* * * * *